US010548946B2

(12) United States Patent
Golden et al.

(10) Patent No.: US 10,548,946 B2
(45) Date of Patent: *Feb. 4, 2020

(54) THERAPEUTIC COMPOSITIONS FOR NEUTRALIZING TYPE I INTERFERONS, AND METHODS OF USE

(71) Applicant: The United States of America, as represented by the Secretary of the Army, on behalf of the United States, Fort Detrick, MD (US)

(72) Inventors: Joseph Golden, Hagerstown, MD (US); Jay Hooper, New Market, MD (US)

(73) Assignee: The government of the United States, as represented by the Secretary of the Army, Fort Detrick, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/828,582

(22) Filed: Dec. 1, 2017

(65) Prior Publication Data

US 2018/0110826 A1 Apr. 26, 2018

Related U.S. Application Data

(63) Continuation of application No. 14/785,058, filed as application No. PCT/US2014/034078 on Apr. 15, 2014, now Pat. No. 9,861,681.

(60) Provisional application No. 61/813,266, filed on Apr. 18, 2013.

(51) Int. Cl.
A61K 38/16 (2006.01)
A61K 39/275 (2006.01)

(52) U.S. Cl.
CPC .................................. A61K 38/162 (2013.01)

(58) Field of Classification Search
CPC ........... C12N 2795/18123; C12N 2730/10123; C12N 15/88; C12N 2710/10322; C12N 2710/10343; C12N 2710/10345; C12N 2770/14023
See application file for complete search history.

(56) References Cited

U.S. PATENT DOCUMENTS

| 5,328,984 | A | 7/1994 | Pastan | |
|---|---|---|---|---|
| 5,668,255 | A | 9/1997 | Murphy | |
| 6,426,042 | B1 | 7/2002 | Asada | |
| 6,451,309 | B2 | 9/2002 | Hooper | |
| 6,562,376 | B2 | 5/2003 | Hooper | |
| 6,620,412 | B2 | 9/2003 | Hooper | |
| 6,773,920 | B1 | 8/2004 | Dalby | |
| 7,083,950 | B2 | 8/2006 | Stahl | |
| 7,217,812 | B2 | 5/2007 | Hooper | |
| 7,285,826 | B2 * | 10/2007 | Doris | H01L 21/823807 257/351 |
| 7,732,167 | B2 | 6/2010 | Smith | |
| 7,790,182 | B2 | 9/2010 | Hooper | |
| 7,887,814 | B2 * | 2/2011 | Maroun | A61K 38/162 424/232.1 |
| 8,092,809 | B2 | 1/2012 | FitzGerald | |
| 8,183,358 | B2 | 5/2012 | Hooper | |
| 8,513,005 | B2 | 8/2013 | Hooper | |
| 8,771,700 | B2 * | 7/2014 | Kotenko | A61K 38/162 424/186.1 |
| 8,852,598 | B2 | 10/2014 | Hooper | |
| 8,883,168 | B2 * | 11/2014 | Hausmann | C07K 14/005 424/199.1 |
| 9,861,681 | B2 * | 1/2018 | Golden | A61K 38/162 |
| 2010/0254981 | A1 | 10/2010 | Sigal | |
| 2011/0027282 | A1 | 2/2011 | Kotenko | |
| 2012/0089076 | A1 | 4/2012 | Thompson | |
| 2014/0079731 | A1 | 3/2014 | Hooper | |

FOREIGN PATENT DOCUMENTS

| WO | WO 1992/007944 | 5/1992 |
|---|---|---|
| WO | WO 2001/058485 | 8/2001 |
| WO | WO 2012/105931 | 8/2001 |
| WO | WO 2001/066138 | 3/2002 |
| WO | WO 2004/058808 | 3/2005 |
| WO | WO 2006/044529 A1 | 4/2006 |
| WO | WO 2007/120368 | 10/2007 |
| WO | WO 2008/100508 | 8/2008 |
| WO | WO 2008/127567 A1 | 10/2008 |
| WO | WO 2009/009039 | 1/2009 |

OTHER PUBLICATIONS

Alcami, A., and G. L. Smith. 1992. A soluble receptor for interleukin-1 beta encoded by Vaccinia virus: a novel mechanism of virus . . . Cell 71:153-67.

Alcami, A., J. A. Symons, and G. L. Smith, 2000. The Vaccinia virus soluble alpha/beta interferon (IFN) receptor binds to the cell surface . . . J Virol 74:11230-9.

Ank, N., H. West, C. Barthoidy, K. Eriksson, A. R. Thomsen, and S. R. Paludan. 2006. Lambda interferon (IFN-lambda), a Type III IFN, is induded . . . J Virol 80:4501-9.

Colamonici, O. R., P. Domanski, S. M. Swietzer, A. Larner, and R. M. Buller. 1995. Vaccinia virus B18R gene encodes a Type I interferon-binding protein . . . J Biol Chem 270:159.

Haller, O., G. Kochs, and F. Weber. 2007. Interferon, Mx, and viral countermeasures. Cytokine Growth Factor Rev 18:425-33.

Haller, O., G. Kochs, and F. Weber. 2006. The interferon response circuit: induction and suppression by pathogenic viruses. Virology 344:119-30.

(Continued)

Primary Examiner — Bao Q Li
(74) Attorney, Agent, or Firm — Leigh Callander

(57) ABSTRACT

The inventions describe here cover therapeutic compositions, and methods of use, for neutralizing Type I interferons in a mammal. The compositions contain a soluble Orthopoxvirus IFN-binding protein that is modified to remove the cell-binding region, and that specifically binds to Type I IFNs, and a pharmaceutically acceptable carrier or excipient. Another variation of the invention entails a novel IFN-binding protein that is modified to remove the cell-binding region and the signal sequence.

10 Claims, 7 Drawing Sheets

Specification includes a Sequence Listing.

(56) References Cited

OTHER PUBLICATIONS

Hooper, J. W., K. I. Kamrud, F. Elgh, D. Custer. and C. S. Schmaljohn. 1999. DNA vaccination with hantavirus M segment elicits neutralizing antibodies . . . Virology 255:269-78.

Kamrud, K. I., J. W. Hooper, F. Elgh, and C. S. Schmaljohn. 1999. Comparison of the protective efficacy of naked DNA, DNA-based Sindbis repilcon, . . . Virology 263:209-19.

Nguyen, D. N., et al., 2009. A novel high-throughput dell-based . . . Biotechnol Bioeng 103:664-75.

Novelli, F., and J. L. Casanova. 2004. The role of IL-12, IL-23 and IFN-gamma in immunity to viruses. Cytokine Growth Factor Rev 15:367-77.

Pestka, S., C. D. Krause, and M. R. Walter. 2004. Interferons, interferon-like cytokines, and their receptors. Immunol Rev 202:8-32.

Symons, J. A., A. Alcami, and G. L. Smith. 1995. Vaccinia virus encodes a soluble Type I interferon receptor of novel structure and broad species specificity. Cell 81:551-60.

Weber, F., G. Kochs, and O. Haller. 2004. Inverse interference: how viruses fight the interferon system. Viral Immunol 17:498-515.

Xu, R. H., et al. 2008. The orthopoxvirus Type I IFN binding protein is essential for virulence and an effective target for vaccination. J Exp Med 205:981-92.

Golden and Hooper 2010. Evaluating the Orthopoxvirus Type I Interferon-Binding Molecule . . . Clinical and Vaccine Immunology vol. 17, No. 11, pp. 1656-1668.

Del Mar Fernandez de Marco, FASE Journal, Research Communication, vol. 24, May 2010, p. 1479-1488.

Presentation by Lee, Ching A., et al., 2010, Washington University (Abstract), Structural basis of Type 1 IFN sequestration by an orthopoxvirus decoy receptor.

Liptakova et al., Virology, 232, pp. 86-90 (1997).

Montanuy et al., FASEB Journal, Research Communication, publ. online Mar. 3, 2011, pp. 1-12.

International Search Report and Written Opinion in parallel application WO 2014/172309, dated Nov. 4, 2014, pp. 1-18.

\* cited by examiner

FIG. 4

SEQUENCE LISTING

```
<160> NUMBER OF SEQ ID NOS: 10

<210> SEQ ID NO 1
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Pro Pro Ser Cys Ile Pro Lys Thr Tyr Glu Leu Gly
    50                  55                  60

Thr His Asp Lys Tyr Gly Ile Asp Leu Tyr Cys Gly Ile Leu Tyr Ala
65                  70                  75                  80

Lys His Tyr Asn Asn Ile Thr Trp Tyr Lys Asp Asn Lys Glu Ile Asn
                85                  90                  95

Ile Asp Asp Ile Lys Tyr Ser Gln Thr Gly Lys Glu Leu Ile Ile His
            100                 105                 110

Asn Pro Glu Leu Glu Asp Ser Gly Arg Tyr Asp Cys Tyr Val His Tyr
        115                 120                 125

Asp Asp Val Arg Ile Lys Asn Asp Ile Val Val Ser Arg Cys Lys Ile
    130                 135                 140

Leu Thr Val Ile Pro Ser Gln Asp His Arg Phe Lys Leu Ile Leu Asp
145                 150                 155                 160

Pro Lys Ile Asn Val Thr Ile Gly Glu Pro Ala Asn Ile Thr Cys Thr
                165                 170                 175

Ala Val Ser Thr Ser Leu Leu Ile Asp Asp Val Leu Ile Glu Trp Glu
            180                 185                 190

Asn Pro Ser Gly Trp Leu Ile Gly Phe Asp Phe Asp Val Tyr Ser Val
        195                 200                 205

Leu Thr Ser Arg Gly Gly Ile Thr Glu Ala Thr Leu Tyr Phe Glu Asn
    210                 215                 220
```

```
Val Thr Glu Glu Tyr Ile Gly Asn Thr Tyr Lys Cys Arg Gly His Asn
225                 230                 235                 240

Tyr Tyr Phe Glu Lys Thr Leu Thr Thr Val Val Leu Glu
                245                 250

<210> SEQ ID NO 2
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Pro Pro Ser Cys Ile Pro Lys Thr Tyr Glu Leu Gly Thr His Asp
1               5                   10                  15

Lys Tyr Gly Ile Asp Leu Tyr Cys Gly Ile Leu Tyr Ala Lys His Tyr
            20                  25                  30

Asn Asn Ile Thr Trp Tyr Lys Asp Asn Lys Glu Ile Asn Ile Asp Asp
        35                  40                  45

Ile Lys Tyr Ser Gln Thr Gly Lys Glu Leu Ile Ile His Asn Pro Glu
50                  55                  60

Leu Glu Asp Ser Gly Arg Tyr Asp Cys Tyr Val His Tyr Asp Asp Val
65                  70                  75                  80

Arg Ile Lys Asn Asp Ile Val Val Ser Arg Cys Lys Ile Leu Thr Val
                85                  90                  95

Ile Pro Ser Gln Asp His Arg Phe Lys Leu Ile Leu Asp Pro Lys Ile
            100                 105                 110

Asn Val Thr Ile Gly Glu Pro Ala Asn Ile Thr Cys Thr Ala Val Ser
        115                 120                 125

Thr Ser Leu Leu Ile Asp Asp Val Leu Ile Glu Trp Glu Asn Pro Ser
130                 135                 140

Gly Trp Leu Ile Gly Phe Asp Phe Asp Val Tyr Ser Val Leu Thr Ser
145                 150                 155                 160

Arg Gly Gly Ile Thr Glu Ala Thr Leu Tyr Phe Glu Asn Val Thr Glu
                165                 170                 175

Glu Tyr Ile Gly Asn Thr Tyr Lys Cys Arg Gly His Asn Tyr Tyr Phe
            180                 185                 190

Glu Lys Thr Leu Thr Thr Val Val Leu Glu
        195                 200

<210> SEQ ID NO 3
<211> LENGTH: 52
<212> TYPE: PRT
<213> ORGANISM: Vaccinia virus

<400> SEQUENCE: 3

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala
50

<210> SEQ ID NO 4
```

<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atgaccatga agatgatggt gcacatctac ttcgtgagcc tgctgctcct gctgttccac      60
agctacgcca tcgacatcga gaacgagatc accgagttct tcaacaagat gcgggacacc     120
ctgccccgcca aggacagcaa gtggctgaac ccgcccccc ccagctgcat ccccaagacc     180
tacgagctgg gcacccacga caagtacggc atcgacctgt actgcggcat cctgtacgcc     240
aagcactaca acaacatcac ctggtataag gacaacaaag agatcaacat cgacgacatc     300
aagtacagcc agaccggcaa agagctgatc atccacaacc ccgagctgga agatagcggc     360
agatacgact gctacgtgca ctacgacgac gtgcggatca gaacgacat cgtggtgtcc      420
cggtgcaaga tcctgaccgt gatccccagc caggaccacc ggttcaagct gatcctggac     480
cccaagatca acgtgaccat cggcgagccc gccaatatca cctgcaccgc cgtgagcacc     540
agcctgctga tcgacgatgt gctgatcgag tgggagaacc ctagcggctg gctgatcggc     600
ttcgacttcg acgtgtacag cgtgctgacc agcaggggcg gcatcaccga ggccaccctg     660
tacttcgaga cgtgaccga ggaatacatc ggcaacacct acaagtgcag gggccacaac     720
tactacttcg aaaagaccct gaccaccacc gtggtgctgg aa                       762
```

<210> SEQ ID NO 5
<211> LENGTH: 609
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
atgccccca gctgcatccc caagacctac gagctgggca cccacgacaa gtacggcatc      60
gacctgtact gcggcatcct gtacgccaag cactacaaca acatcacctg gtataaggac     120
aacaaagaga tcaacatcga cgacatcaag tacagccaga ccggcaaaga gctgatcatc     180
cacaaccccg agctggaaga tagcggcaga tacgactgct acgtgcacta cgacgacgtg     240
cggatcaaga cgacatcgt ggtgtcccgg tgcaagatcc tgaccgtgat ccccagccag      300
gaccaccggt tcaagctgat cctggacccc aagatcaacg tgaccatcgg cgagcccgcc     360
aatatcaccct gcaccgccgt gagcaccagc ctgctgatcg acgatgtgct gatcgagtgg     420
gagaacccta gcggctggct gatcggcttc gacttcgacg tgtacagcgt gctgaccagc     480
aggggcggca tcaccgaggc caccctgtac ttcgagaacg tgaccgagga atacatcggc     540
aacacctaca gtgcagggg ccacaactac tacttcgaaa agaccctgac caccaccgtg      600
gtgctggaa                                                            609
```

<210> SEQ ID NO 6
<211> LENGTH: 156
<212> TYPE: DNA
<213> ORGANISM: Vaccinia virus

<400> SEQUENCE: 6

```
atgaccatga agatgatggt gcacatctac ttcgtgagcc tgctgctcct gctgttccac      60
agctacgcca tcgacatcga gaacgagatc accgagttct tcaacaagat gcgggacacc     120
```

```
ctgcccgcca aggacagcaa gtggctgaac cccgcc                                  156
```

<210> SEQ ID NO 7
<211> LENGTH: 486
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgaccatga agatgatggt gcacatctac ttcgtgagcc tgctgctcct gctgttccac     60
agctacgcca tcgacatcga gaacgagatc accgagttct tcaacaagat gcgggacacc    120
ctgcccgcca aggacagcaa gtggctgaac cccgcctgca tgttcggcgg caccatgaac    180
gatatcgccg ccctgggcga gcccttcagc gccaagtgcc cccccatcga ggacagcctg    240
ctgtcccacc ggtacaagga ctacgtggtg aagtgggagc ggctggaaaa gaaccggcgg    300
aggcaggtgt ccaacaagag agtgaagcac ggcgacctgt ggatcgccaa ctacaccagc    360
aagttcagca accggcgcta cctgtgcacc gtgaccacca gaacggcga ctgcgtgcag    420 ggcatcgtgc ggagccacat ccggaagccc cccagctgca tccccaagac ctacgagctg    480
ggcacc                                                               486
```

<210> SEQ ID NO 8
<211> LENGTH: 162
<212> TYPE: PRT
<213> ORGANISM: Vaccinia virus

<400> SEQUENCE: 8

```
Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr
```

<210> SEQ ID NO 9
<211> LENGTH: 4331
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 9

| | | | | | |
|---|---|---|---|---|---|
| gggggggggg | ggcgctgagg | tctgcctcgt | gaagaaggtg | ttgctgactc | ataccaggcc | 60 |
| tgaatcgccc | catcatccag | ccagaaagtg | agggagccac | ggttgatgag | agctttgttg | 120 |
| taggtggacc | agttggtgat | tttgaacttt | tgctttgcca | cggaacggtc | tgcgttgtcg | 180 |
| ggaagatgcg | tgatctgatc | cttcaactca | gcaaaagttc | gatttattca | acaaagccgc | 240 |
| cgtcccgtca | agtcagcgta | atgctctgcc | agtgttacaa | ccaattaacc | aattctgatt | 300 |
| agaaaaactc | atcgagcatc | aaatgaaact | gcaatttatt | catatcagga | ttatcaatac | 360 |
| catattttg | aaaagccgt | ttctgtaatg | aaggagaaaa | ctcaccgagg | cagttccata | 420 |
| ggatggcaag | atcctggtat | cggtctgcga | ttccgactcg | tccaacatca | atacaaccta | 480 |
| ttaatttccc | ctcgtcaaaa | ataaggttat | caagtgagaa | atcaccatga | gtgacgactg | 540 |
| aatccggtga | gaatggcaaa | agcttatgca | tttctttcca | gacttgttca | acaggccagc | 600 |
| cattacgctc | gtcatcaaaa | tcactcgcat | caaccaaacc | gttattcatt | cgtgattgcg | 660 |
| cctgagcgag | acgaaatacg | cgatcgctgt | taaaaggaca | attacaaaca | ggaatcgaat | 720 |
| gcaaccggcg | caggaacact | gccagcgcat | caacaatatt | ttcacctgaa | tcaggatatt | 780 |
| cttctaatac | ctggaatgct | gttttcccgg | ggatcgcagt | ggtgagtaac | catgcatcat | 840 |
| caggagtacg | gataaaatgc | ttgatggtcg | gaagaggcat | aaattccgtc | agccagttta | 900 |
| gtctgaccat | ctcatctgta | acatcattgg | caacgctacc | tttgccatgt | tcagaaaaca | 960 |
| actctggcgc | atcgggcttc | ccatacaatc | gatagattgt | cgcacctgat | tgcccgacat | 1020 |
| tatcgcgagc | ccatttatac | ccatataaat | cagcatccat | gttggaattt | aatcgcggcc | 1080 |
| tcgagcaaga | cgtttcccgt | tgaatatggc | tcataacacc | ccttgtatta | ctgtttatgt | 1140 |
| aagcagacag | ttttattgtt | catgatgata | tatttttatc | ttgtgcaatg | taacatcaga | 1200 |
| gattttgaga | cacaacgtgg | ctttcccccc | cccccggca | tgcctgcagg | tcgacataaa | 1260 |
| tcaatattgg | ctattggcca | ttgcatacgt | tgtatctata | tcataatatg | tacatttata | 1320 |
| ttggctcatg | tccaatatga | ccgccatgtt | gacattgatt | attgactagt | tattaatagt | 1380 |
| aatcaattac | ggggtcatta | gttcatagcc | catatatgga | gttccgcgtt | acataactta | 1440 |
| cggtaaatgg | cccgcctcgt | gaccgcccaa | cgacccccgc | ccattgacgt | caataatgac | 1500 |
| gtatgttccc | atagtaacgc | caatagggac | tttccattga | cgtcaatggg | tggagtattt | 1560 |
| acggtaaact | gcccacttgg | cagtacatca | agtgtatcat | atgccaagtc | cggcccccta | 1620 |
| ttgacgtcaa | tgacggtaaa | tggcccgcct | ggcattatgc | ccagtacatg | accttacggg | 1680 |
| actttcctac | ttggcagtac | atctacgtat | tagtcatcgc | tattaccatg | gtgatgcggt | 1740 |
| tttggcagta | caccaatggg | cgtggatagc | ggtttgactc | acggggattt | ccaagtctcc | 1800 |
| accccattga | cgtcaatggg | agtttgtttt | ggcaccaaaa | tcaacgggac | tttccaaaat | 1860 |
| gtcgtaataa | ccccgcccg | ttgacgcaaa | tgggcggtag | gcgtgtacgg | tgggaggtct | 1920 |
| atataagcag | agctcgttta | gtgaaccgtc | agatcgcctg | gagacgccat | ccacgctgtt | 1980 |
| ttgacctcca | tagaagacac | cgggaccgat | ccagcctccg | cggccgggaa | cggtgcattg | 2040 |
| gaacgcggat | tccccgtgcc | aagagtgacg | taagtaccgc | ctatagactc | tataggcaca | 2100 |
| cccctttggc | tcttatgcat | gctatactgt | ttttggcttg | ggcctatac | accccgctc | 2160 |
| cttatgctat | aggtgatggt | atagcttagc | ctataggtgt | gggttattga | ccattattga | 2220 |
| ccactcccct | attggtgacg | atactttcca | ttactaatcc | ataacatggc | tctttgccac | 2280 |

```
aactatctct attggctata tgccaatact ctgtccttca gagactgaca cggactctgt    2340
atttttacag gatggggtcc catttattat ttacaaattc acatatacaa caacgccgtc    2400
ccccgtgccc gcagttttta ttaaacatag cgtgggatct ccacgcgaat ctcgggtacg    2460
tgttccggac atgggctctt ctccggtagc ggcggagctt ccacatccga gccctggtcc    2520
catgcctcca gcggctcatg gtcgctcggc agctccttgc tcctaacagt ggaggccaga    2580
cttaggcaca gcacaatgcc caccaccacc agtgtgccgc acaaggccgt ggcggtaggg    2640
tatgtgtctg aaaatgagct cggagattgg gctcgcaccg tgacgcagat ggaagactta    2700
aggcagcggc agaagaagat gcaggcagct gagttgttgt attctgataa gagtcagagg    2760
taactcccgt tgcggtgctg ttaacggtgg agggcagtgt agtctgagca gtactcgttg    2820
ctgccgcgcg cgccaccaga cataatagct gacagactaa cagactgttc ctttccatgg    2880
gtcttttctg cagtcaccgt ccaagcttgc ggccgcggat cctcgcaatc cctaggagga    2940
ttaggcaagg gcttgagctc acgctcttgt gagggacaga aatacaatca ggggcagtat    3000
atgaatactc catggagaaa cccagatcta cgtatgatca gcctcgactg tgccttctag    3060
ttgccagcca tctgttgttt gccctcccc cgtgccttcc ttgaccctgg aaggtgccac    3120
tcccactgtc ctttcctaat aaaatgagga aattgcatcg cattgtctga gtaggtgtca    3180
ttctattctg ggggtgggg tgggcagga cagcaagggg gaggattggg aagacaatag    3240
caggcatgct ggggatgcgg tgggctctat ggcttctgag gcggaaagaa ccagctgggg    3300
ctcgacagct cgactctaga attgcttcct cgctcactga ctcgctgcgc tcggtcgttc    3360
ggctgcggcg agcggtatca gctcactcaa aggcggtaat acggttatcc acagaatcag    3420
gggataacgc aggaaagaac atgtgagcaa aaggccagca aaaggccagg aaccgtaaaa    3480
aggccgcgtt gctggcgttt ttccataggc tccgccccc tgacgagcat cacaaaaatc    3540
gacgctcaag tcagaggtgg cgaaacccga caggactata agataccagg cgtttcccc    3600 ctggaagctc cctcgtgcgc tctcctgttc cgaccctgcc gcttaccgga tacctgtccg    3660
cctttctccc ttcgggaagc gtggcgcttt ctcaatgctc acgctgtagg tatctcagtt    3720
cggtgtaggt cgttcgctcc aagctgggct gtgtgcacga accccccgtt cagcccgacc    3780
gctgcgcctt atccggtaac tatcgtcttg agtccaaccc ggtaagacac gacttatcgc    3840
cactggcagc agccactggt aacaggatta gcagagcgag gtatgtaggc ggtgctacag    3900
agttcttgaa gtggtggcct aactacggct acactagaag gacagtattt ggtatctgcg    3960
ctctgctgaa gccagttacc ttcggaaaaa gagttggtag ctcttgatcc ggcaaacaaa    4020
ccaccgctgg tagcggtggt ttttttgttt gcaagcagca gattacgcgc agaaaaaaag    4080
gatctcaaga agatcctttg atcttttcta cggggtctga cgctcagtgg aacgaaaact    4140
cacgttaagg gattttggtc atgagattat caaaaaggat cttcacctag atccttttaa    4200
attaaaaatg aagttttaaa tcaatctaaa gtatatatga gtaaacttgg tctgacagtt    4260
accaatgctt aatcagtgag gcacctatct cagcgatctg tctatttcgt tcatccatag    4320
ttgcctgact c                                                        4331
```

<210> SEQ ID NO 10  
<211> LENGTH: 6  
<212> TYPE: PRT  
<213> ORGANISM: Artificial Sequence  
<220> FEATURE:  
<223> OTHER INFORMATION: Description of Artificial Sequence: Synthetic 6xHis tag

```
<400> SEQUENCE: 10

His His His His His His
1               5
```

THERAPEUTIC COMPOSITIONS FOR NEUTRALIZING TYPE I INTERFERONS, AND METHODS OF USE

This application claims priority from prior U.S. provisional application 61/813,266, filed Apr. 18, 2013, the entire contents of which are hereby incorporated by reference.

FIELD OF THE INVENTION

The invention is a novel composition for therapeutic purposes, specifically for reducing or controlling amounts of Type I interferons in a subject. The compositions contain a modified Orthopoxvirus Type I interferon-binding protein (IFN-binding protein), which neutralizes Type I interferons by binding specifically thereto, in vivo and in vitro. The invention encompasses these novel therapeutic compositions containing the modified protein, and methods of their use.

BACKGROUND OF THE INVENTION

Type I interferons (IFN) are critical components of the innate immune responses, in particular defense against viral infection (7, 12, 20). Paradoxically, excessive amounts of type I IFN produced from a variety of insults, including viral infection (5, 16, 22, 25) and bacterial sepsis (4, 14) can lead to significant pathology from acute inflammation (17, 21, 23). Recently, type I IFN has been shown to drive tumor necrosis factor (TNF) lethal shock (11, 28). Thus, excessive amounts of type I IFN can have negative consequences for the host driving acute inflammation that may ultimately lead to organ failure and death (15, 25). Plato best illustrated the point: "Excess generally causes reaction, and produces a change in the opposite direction . . . ." In fact, some have called for therapeutics that neutralize type I IFNs in the treatment of inflammatory diseases, including sepsis (15, 25).

Interferons (IFNs) are proteins produced in mammals, useful as antiviral agents and for fighting tumors. Interferons (IFNs) are host defense molecules and consist of three classes, Type I, Type II and recently identified Type III. Type I IFNs including the prototypical members IFN-alpha and IFN-beta. Type I IFNs are involved in the generation of an antiviral state to help limit the spread of viruses (11) (see reference list below). The Type II class of IFNs consists solely of IFN-gamma and is predominately involved in shaping the Th1 arm of the T-cell response (10). Type III IFNs consist of IFN-lamba and have a function believed to be similar to Type I IFNs, though they signal through different receptors (3).

IFNs are potent inactivators of viral replication within infected hosts and accordingly, are key components in host defense against infection (5, 6, 13). Not surprisingly, viruses have evolved complex systems to defeat these antiviral molecules. These mechanisms include intracellular systems such as the V protein of paramyxoviruses SV5, which inhibits IFN function by targeting RIG-1-related RNA sensor MDA-5 (6). Other viruses have developed IFN-binding molecules that directly interact with IFN and neutralize its activity.

Interferons have been used to boost immune effects against several diseases, including actinic keratosis, superficial basal cell carcinoma, papilloma and external genital warts. Synthetic IFNs are also made, and administered as antiviral, antiseptic and anticarcinogenic drugs, and to treat some autoimmune diseases (e.g., Multiple sclerosis). Interferon beta-1a and interferon beta-1b are used to treat and control multiple sclerosis, an autoimmune disorder. Both hepatitis B and hepatitis C are treated with IFN-α. Interferon therapy is used as a treatment for many cancers, especially hematological malignancy; leukemia and lymphomas including hairy cell leukemia, chronic myeloid leukemia, nodular lymphoma, cutaneous T-cell lymphoma. When used in the systemic therapy, IFNs are mostly administered by an intramuscular injection.

Recent findings suggest that interferon may boost the specific immune system response against the influenza virus. A flu vaccine that uses interferon as adjuvant is currently under clinical trials in the US.

One of the problems associated with IFN therapy is the large amount needed for effective treatment. For example, Interleukin-2 used to keep Hep C virus levels down in Hep C patients can result in the production of massive amounts of interferon. This over production of interferon causes severe and even life threatening adverse effects. Debilitating side effects can include flu-like symptoms, increased body temperature, feeling ill, fatigue, headache, muscle pain, convulsion, dizziness, hair thinning, and depression. Erythema, pain and hardness on the spot of injection are also frequently observed. Other side effects are life-threatening: heart attack, stroke, enhancement of autoimmune disorder Patients might even refuse treatment with recombinant IFN-alpha and/or IL-2 because of the severe side effects.

Certain conditions and diseases are known to cause overproductions of interferon. This is true for viral infections (influenza, RSV, viral hemorrhagic fever viruses), autoimmune disorders (lupus), bacterial infections (any causing septic shock, *E coli*, hemophilus influenza, *Yersina Pestis*, etc.

In the scientific community, there is growing recognition for the concept that neutralizing Type I interferons to negate pathogenic effects of both infectious and noninfectious (autoimmune) disease can be beneficial. However, there is currently no IFN-neutralizing therapeutic medicine or treatment that is safe and can be easily regulated. Type I IFNs constitute a constellation of molecules that include the prototypical IFN-alpha and beta as well as IFN-kappa and IFN-epsilon. In addition to these broad categories, IFN-alpha is subdivided into a multiple of IFNs which include 13 subtypes in humans. All type I IFNs signal through the type I IFN receptor. Because of the large number of type I IFNs, it is difficult to generate a product that broadly targets the entire family. Antibodies generally only bind one or type subtypes. A product that could inhibit/neutralize both IFN-alpha (and subtypes) and IFN-beta, as well as the other type I IFNs could have an advantage in terms of efficacy. Additionally, there is a large species specificity among type I IFNs, thus products that work in humans may not function effectively in mice, or other animals. This may hinder research and development. A broadly neutralizing, non-species specific product that can be used to control deleterious effects of type I IFNs in vivo is desired.

SUMMARY OF THE INVENTION

The inventors have found compositions and methods effective for neutralizing Type I interferons in a patient, so as to negate pathogenic effects of both infectious and non-infectious (autoimmune) diseases. Specifically, we have developed a therapeutic composition that, in pharmacologically effective amounts, is useful and effective to neutralize, reduce, control or moderate Type I IFNs, to the extent desired, in a mammalian subject. That is, some or many Type I IFNs within the mammal are rendered ineffective or at least less effective to cause inflammation or other negative side effects. Thus, our invention has broad application in medicine to neutralize a harmful inflammatory response by controlling Type I IFN levels under conditions where reduction of these levels would be more beneficial to the subject.

The IFN-binding protein has been characterized a having three regions: a secretion signal, a cell binding region, and an IFN-binding region. The cell binding region and the IFN-binding regions are immunoglobulin-like domains, where the cell-binding region has a first Ig-like domain, and the IFN-binding region has a second and third Ig-like domain.

The composition comprises an isolated soluble Orthopoxvirus IFN-binding protein that is modified to remove the cell-binding region, and that specifically binds to and neutralizes Type I IFNs, and a pharmaceutically acceptable carrier. Put another way, the modified IFN-binding protein includes the IFN-binding region (IBR) and the signal sequence, but not the cell-binding region. Once bound by the modified IFN-binding protein, the IFN is neutralized and no longer effective to cause or contribute to inflammation or any other function within the mammal's body.

Preferably, the modified IFN-binding protein has the amino acid sequence of SEQ ID NO:1. This sequence is derived from the Vaccinia virus B19 IFN-binding protein, and contains the IFN-binding region and the signal sequence. The full-length B19 sequence is well-known, for instance, as described in U.S. Patent Publication No. US2010-0254981. The IFN-binding protein may be a homolog of SEQ ID NO:1, as long as there is 80%, and preferably 90%, homology at the amino acid level. Homology should exist to the extent that the polypeptide binds IFN. We note that the Vaccinia Virus B19 is the same as the protein known as B18, and the only difference is that the source is a different strain of Vaccinia Virus. For example, the IFN-binding proteins of other orthopoxviruses having homology of at least 80% amino acid sequence identity would be suitable for the methods of this invention.

The invention includes an isolated nucleic acid that encodes a modified Type I IFN-binding protein or polypeptide—which contains the IFN-binding region and the signal sequence, but not the cell-binding region—or a fragment, homolog, analog, fusion protein, peptidomimetic or derivative. For example, the nucleic acid can encode a polypeptide of at least 80%, 85%, 90%, 95% or 100% identity to a polypeptide comprising, consisting essentially of, or consisting of the amino acid sequence SEQ ID NO:1, or a portion of it. The nucleic acid can be, for example, a genomic DNA fragment or a cDNA molecule that includes the nucleic acid sequence of SEQ ID NO: 4 or a portion of it. The homologous nucleic acid has at least 70%, 75%, 80%, 85%, 90%, 95% or 100% homology to SEQ ID NO: 4, or a portion of it.

The Orthopoxvirus can be any of Vaccinia virus, camelpox virus, ectromelia virus, raccoon poxvirus, skunk poxvirus, Tatera poxvirus, Uasin Gishu virus, Volepox virus, variola virus, Vaccinia monkeypox virus, and cowpox virus. Due to the high homology between orthopoxviruses, orthologs of the Vaccinia B19 Type I IFN-binding protein that share 80% identity with the amino acid sequence of the B19, may be used as the IFN-binding protein that is modified.

In this invention, the term "ortholog" denotes the well-known meaning of this term. In this art, orthologs are genes in different species which evolved from a common ancestral gene. Due to their separation following a speciation event, orthologs may diverge, but usually have similarity at the sequence and structure levels; furthermore, orthologs usually have identical functions. Orthology is a type of homology. In this application, the term ortholog is used to include the ortholog gene (DNA or RNA) or the peptide/protein product of the ortholog. Sometimes the peptide/protein product of the ortholog is referred to as "ortholog product" or simply "ortholog". The meaning is evident from the context (e.g., a protein vaccine or immunogenic composition will contain peptides or proteins that may be referred to as orthologs—that is, products of an ortholog gene—of another poxvirus; a nucleic acid vaccine will contain nucleic acids that may be referred to as orthologs of another poxvirus—that is, an ortholog gene).

The ortholog products having 80% identity are preferably derived from an orthopoxvirus selected from the group consisting of: camelpox virus, ectromelia virus, raccoon poxvirus, skunk poxvirus, Tatera poxvirus, Uasin Gishu virus, Volepox virus variola virus, Vaccinia virus, monkeypox virus, gerbilpox and cowpox virus, or any genetically modified orthopoxvirus which contains a homolog of the IFN-binding protein that is to be modified (or an engineered IFN-binding protein retaining sufficient homology to retain neutralizing epitopes but lacking the cell-binding feature of the naturally occurring molecule).

In the context of all embodiments of this invention as described herein, these therapeutic compositions are based on recombinant DNA, proteins or peptides that, when administered to a person or mammal, confer or cause a desired treatment, alleviation of existing harmful or undesired effects, or effect results in the recipient that are desirable and beneficial. (By "peptides" it is meant an amino acid sequence that is less than the full-length protein sequence.) The therapeutic compositions described herein have broad application, since IFNs play a role in many contexts within medical conditions and treatments. For the purposes of this invention, changes effected by our therapeutic compositions which are viewed as desirable, given the situation, are called therapeutic.

For purposes of understanding the various embodiments of this invention, by "IFN-binding region" it is meant the region of the IFN-binding protein that functions to bind Type I IFNs, which contains two immunoglobulin-like domains. The IFN-binding regions interacts with Type I IFNs to the extent that it renders the ability of Type I IFNs to interact with endogenous Type I IFN receptors ineffective. This consequently thwarts signaling and reduces or eliminates any subsequent Type I IFN-responses within the host.

By "cell-binding region" it is meant the region of the IFN-binding protein that functions to bind the IFN-binding protein to cell surfaces, and which contains one immunoglobulin-like domain.

By "signal sequence" it is meant the sequence of the protein that contains the secretion signal needed to send the translated peptide or protein through the proper organelles (ER and golgi) where post-translation modifications and folding may occur and then direct the protein or peptide out of the host cell through a secretion pathway. The secretion signal is encoded by a DNA sequence located on the 5' region of the gene that encodes the IFN-binding protein. In the Vaccinia virus B18/B19 protein, the signal sequence has the amino acid sequence of SEQ ID NO:3, which is MTM-KMMVHIYFVSLLLLLFHSYAIDIENEITEFFNK-MRDTLPAKDS KWL NPA (which is amino acids 1-52 of the full protein, and includes the M start codon). This signal sequence is nearly identical in all orthologs.

By "specifically binds" it is meant that a composition is effective to selectively bind another molecule, such as the IFN-binding protein that selectively binds Type I IFNs in vivo or in vitro.

The term "Type I IFNs" is will known in the art, and would be understood by someone having ordinary skill in this art, especially from the context it is used herein.

By "neutralize" is it meant the binding of Type I IFNs in a manner that inhibits or reduces or prevents ability of IFN molecules from, or otherwise interferes with, normal IFN activity—that is, IFN molecules interacting with host IFN-receptors and initiating their normal physiological responses (e.g., preventing cell signaling from the Type I IFN receptor).

By "therapeutic" it is meant the treating or curing of a medical condition, disease or symptom, and generally the consequence of a medical treatment of any kind, the results of which are judged to be desirable and beneficial. To that end, the therapeutic composition of this invention is especially useful where a mammal is producing or in the condition of having elevated or toxic levels of IFNs within the body. For instance, this condition can occur in connection with or be caused by systemic inflammatory response syndrome, autoimmune disease, inflammation and/or sepsis caused by infectious agents, ischemic reperfusion injuries and pathological inflammation. Other causes are when IFNs are injected into the body for medicinal reasons, such as to treat hepatitis C. While IFNs can be effective to treat such conditions, if the level of IFNs exceeds what the body can tolerate (e.g., causing negative side effects), our therapeutic compositions can be administered in appropriate amounts to bring down IFNs to more tolerable levels.

By "therapeutically effective" it is meant capable of achieving a therapeutic objective.

By "high levels of Type I IFNs" is it meant levels exceeding physiological benefit to the host and contributing to host pathology, or otherwise undesirable levels of Type I IFNs. This includes but is not limited to actual overproduction of IFNs by a mammal. As would be understood by persons having ordinary skill in this art, these levels vary with the particular condition, cause or disease. There are well-known methods in the art to test or evaluate levels of Type I IFNs in a body For example, ELISAs have been developed to quantitate the levels of IFN in a host. Levels that begin to be dangerous vary from person to person, but generally systemic inflammatory response syndromes (too much inflammatory cytokines including type I IFN) are easily diagnosed in a hospital setting. One would not have to measure type I IFNs directly, but other markers of inflammation (TNF-alpha, C-reactive protein, multiple organ failure, coagulation disorders, fever, tachycardia, white blood cell counts, bacteremia, viremia, or a combination of all). Once it is determined a person is suffering from an inflammatory condition that is dangerous, inhibition of type I IFNs could be started to try and limit the amount of inflammation.

It is important that the modified protein be soluble because this will allow it to diffuse throughout the host and not bind to cells at the injection site. In contrast to our invention, the naturally occurring IFN-binding proteins that contain the cell-binding region (such as B18/B19) will bind to mammalian cells and are therefore effectively removed from solution in the presence of cells. Or perhaps even worse, they will remain active in the host for a longer period of time where they can inhibit type I IFNs in an unintended, uncontrolled manner. Our therapeutic composition, which is soluble, will not bind cells, and therefore should be removed from circulation in a shorter period of time. The naturally occurring IFN-binding proteins bind to cell surfaces and are therefore not fully soluble within a host. It is noted that sometimes the native IFN-binding protein is referred to as both soluble and cell-binding; however, because it binds cells, or is capable of binding cells, it is only soluble in a very localized area in the host, e.g., the immediately surrounding cells. There can be no systemic spreading of the native IFN-binding protein. To that end, in the context of this invention, by "soluble" it is meant that the composition does not become immobilized by binding to cell surfaces.

Solubility of the modified protein gives rise to two advantages. First, the molecule will more freely and quickly distribute within the host and allow more dissemination within the host. Second, the protein will be cleared more easily from the host body, which may be advantageous if there is a desire to rapidly stop neutralization of the IFNs in the body of the mammal patient/recipient. One of the novel aspects of our invention is that it is reasonably easy to regulate the rate that the IFNs are being neutralized within the recipient's body. The naturally occurring molecule does not have this capability as it binds to cells and potentially could remain active within the host well after the treatment effect has occurred. In fact, this remaining activity may be deleterious in that it will actually prevent a desired Type I IFN response within the host. That is, the lingering cell-bound IFN-binding protein can inhibit future desired IFN response (e.g., to arrest infections in the normal course).

An advantage of our therapeutic compositions and methods is that they permit rapid and controlled neutralizing of type I IFNs, and clear out of the host system rapidly as well. In our methods of use, preventing neutralization will be key to an effective treatment strategy designed to mitigate the negative effects of too much IFN, but also balance the positive effects of having an appropriate amount of IFN present to prevent dangerous infections.

The pharmaceutically acceptable carrier or excipient can be any biologically compatible medium. For instance, the pharmaceutically acceptable carrier may be an isotonic solution suitable for administration of pharmacologic substances into mammals. Alternatively, the modified protein may be suspended in a solvent (such as DMSO) and water. Any known and compatible excipient would be useful, as would be understood by someone having ordinary skill in this art.

Because IFNs are so important and involved in a body's immune response, there are many applications of our therapeutic compositions. In another embodiment, our invention encompasses methods to therapeutically reduce harmful effects in a mammal incurred by high levels of Type I IFNs. The main essential method step is to administer to the mammal one of the therapeutic compositions described herein (i.e., containing an isolated soluble Orthopoxvirus IFN-binding protein that is modified to remove the cell-binding region, and that specifically binds to and neutralizes Type I IFNs, and a pharmaceutically acceptable carrier or excipient), under conditions that the IFN-binding protein binds and neutralizes Type I IFNs in the mammal—and thereby, of course, high levels of IFN are reduced. In general, for this embodiment, it is important that the modified IFN-binding protein include the signal sequence. This is because the modified protein must fold in a manner that allows it to interact with type I IFNs and inhibit/neutralize their activity. Different species, (bacteria cells, mammalian cells and insect cells) have different mechanisms for protein folding, including species specific modifications that can greatly impact the function of a protein. This modified protein appears to fold best in mammalian cells and therefore it is preferred to express it in this cell type. The use of the native signal sequence is most preferred because it assures that the peptide further traffics to the proper compartments within mammalian cells and fold naturally. While it is possible to remove the signal sequence and replace it with another (tPA secretion signal or IgG kappa leader sequence) this is less preferred since it could disrupt the molecule such that it has less potency (i.e., less binding of IFN). The most preferred expression mechanism is mammalian cells, with the native signal sequence and Ig-like domains 2 and 3.

Preferably, once administered, the IFN-binding protein diffuses systemically in the mammal.

The mammal can be a human, or domestic animal.

The composition may be administered by any known means that would be appropriate for the recipient, for instance, parenterally (including injection and the like), by aerosol, infusion or orally.

Our methods would be effective to treat or cause beneficial results whenever a human or other mammal has undesirably high levels of Type I IFNs. Such a condition may be caused or related to systemic inflammatory response syndrome, autoimmune disease, inflammation and/or sepsis caused by infectious agents (e.g., bacteria, viruses, parasites and fungi), ischemic reperfusion injuries and pathological inflammation or any injury or medical condition resulting in inflammation that is deleterious to the host. Other causes of undesirably high levels of Type I IFNs are certain medicines, such as a medicine for Hepatitis C (e.g., Pegintron) or a medicine containing IFN or IFN-based products, or biosimilars. Recombinant Type I IFN (such as Pegintron, which is recombinant Type I IFN alpha) and interleukin-2 are common pharmaceuticals that can produce excessive IFN. Unfortunately, IFN levels may even become dangerously high. Our therapeutic compositions may be administered when IFN levels become too high.

In a related embodiment, our invention covers methods to modulate or regulate (e.g., down-regulate) IFN responses or activity. In a mammalian subject that is believed to have an excessive level of IFNs, it is desirable and possibly essential to lower the level of IFNs in a safe and controlled manner. It is important that the level of IFNs do not go too low. In this method, IFN response or activity is modulated or regulated by contacting mammalian cells (e.g., by any of the ways listed for administration) with one of the therapeutic compositions described here, in a sufficient amount to modulate IFN response or activity, under conditions that the modified IFN-binding protein specifically binds to and neutralizes IFN in the mammal. The therapeutic compositions described here can be administered to a mammalian subject in pharmacologically effective doses as needed to regulate the amount of IFNs in the mammal, in a controlled way. The level of IFNs is assessed by known medical methods, and when the desired level of IFNs is reached in the subject, the administration of the therapeutic composition is stopped. This embodiment is advantageous because the modified IFN-binding protein is very specific to bind IFNs, and little time is needed for the desired effects to take place once it is administered. One example is recombinant Type I IFN-alpha (brand name: PegIntron, or any variety of pegalated type I IFN-alpha), such as when given as medicine for Hepatitis C. Another example is IFN-beta which is administered for treatment of multiple sclerosis.

In a different embodiment, the invention covers another isolated soluble Orthopoxvirus Type 1 IFN-binding protein, but this one is modified to remove both the cell-binding region and the signal sequence. This modified protein specifically binds to and neutralizes Type I IFN. Unlike the modified IFN-binding protein described above, this embodiment does not contain the signal sequence—it only contains the interferon binding region (IBR). Preferably, this embodiment of the modified IFN-binding protein has the amino acid sequence of SEQ ID NO:2, which corresponds to the IBR in the Vaccinia virus B19 protein.

This embodiment of the invention also includes an isolated nucleic acid that encodes this modified Type I IFN-binding protein or polypeptide—which contains the IFN-binding region but not the signal sequence of the cell-binding region—or a fragment, homolog, analog, fusion protein, peptidomimetic or derivative. For example, the nucleic acid can encode a polypeptide of at least 80%, 85%, 90%, 95% or 100% identity to a polypeptide comprising, consisting essentially of, or consisting of the amino acid sequence SEQ ID NO:2, or a portion of it. The nucleic acid can be, for example, a genomic DNA fragment or a cDNA molecule that includes the nucleic acid sequence of SEQ ID NO:5 or a portion of it. The homologous nucleic acid has at least 80%, 85%, 90%, 95% or 100% homology to SEQ ID NO:5, or a portion of it.

As described above for the other modified IFN-binding protein (which contains the signal sequence), the IFN-binding protein (without the signal sequence) may be a homolog of SEQUENCE ID NO:2. For example, the IFN-binding proteins of other orthopoxviruses having homology of at least 80% amino acid sequence identity would be suitable for the methods of this invention. The Orthopoxiviruses contemplated for this embodiment are noted above.

In particular, this embodiment without the signal sequence has the advantage that the DNA sequence can be inserted into a non-mammalian expression system and expressed in large quantities. The E. coli expression system is useful for this, and the E. coli signal sequence was effective to operably express the inserted DNA sequence.

It is well known that signal sequences can be functionally interchangeable even between different species. Other "foreign" secretion signal sequences that would be useful include bacterial, yeast, fungi, and insect, as well as other mammalian expression systems. These foreign signal sequences can be operably linked to the modified IFN-binding protein using methods well known in the art. Specifically regarding mammalian cells, any mammalian expression system would be compatible if it contained a secretion signal, the stop codon (e.g., tPA-secretion signal and Ig kappa chain leader sequence), and other known required components. An advantage of a mammalian expression system is that the expressed peptide will fold properly and get secreted normally—thus, taking the place of the natural secretion signal sequence.

As described below, the inventors found that the modified IFN-binding protein without the signal sequence, when expressed in E. coli, resulted in a reduced capacity to neutralize Type I IFN—this is believed to be because the modified protein was expressed in a non-mammalian expression system (using the mammalian signal sequence), and the expression product did not fold as properly or effectively as the product of the mammalian expression system (using the mammalian signal sequence). It is likely that differences in protein processing resulted in a molecule with decreased capacity to bind Type I IFN. However, binding was sufficient for purposes of neutralizing Type I IFNs in an in vitro assay, but required significantly more protein for effect (more than a 10-fold reduction). Expressing this modified IFN-binding protein in an E. coli expression system resulted in a product that is not as specifically binding as the IBR with the signal sequence, but is effective to binding IFNs in a mammalian subject.

In another embodiment, the invention encompasses a DNA cassette that is capable of being cloned into a delivery system. The DNA cassette comprises (1) the DNA sequence of any of the modified IFN-binding protein described above (in any of its variations and orthologs, including SEQ ID NO:4 and SEQ ID NO:5) (2) linked to a promoter or an internal ribosome entry site operable in a expression system (eukaryotic or prokaryotic, as appropriate), and (3) operably linked to a start codon, at least one stop codon and a poly adenylation (polyA) sequence. As is well known, the poly A sequence is critical for efficient expression, and is placed on the 3' end of the gene, after the stop codon. Where the DNA sequence includes both the sequence for IFN-binding protein and signal sequence (such as SEQ ID NO:1), the most preferred delivery system is a mammalian expression plasmid (such as pWRG). In the mammalian cells, the IFN-binding protein is expressed and folds more properly than in non-mammalian cells.

However, where the DNA sequence includes the sequence for IFN-binding protein, and not the signal sequence (such as SEQ ID NO:2), the most preferred delivery system is non-mammalian. The signal sequence of the naturally-occurring IFN-binding protein (e.g. DNA sequence SEQ ID NO:6) is ineffective in non-mammalian cells because it won't be removed (as happens naturally in mammalian cells). Therefore, in this embodiment the DNA sequence can be inserted into currently available expression vectors and expressed in bacterial (e.g., *E. coli*), insect or yeast. In these non-mammalian expression systems, the modified IFN-binding protein is expressed and does fold but not always as properly and effectively as when expressed in the mammalian cells. The result of this inefficient or incorrect folding is a molecule with reduced capacity to neutralize type I IFN (e.g., can be a greater than 10-fold decrease over mammalian expressed systems).

In a related embodiment, the invention entails a DNA construct or plasmid comprising a vector, and the DNA sequence of the modified IFN-binding protein described above (in any of its variations and orthologs). The sequence of a preferred expression plasmid is listed below, as SEQ ID NO:9. This sequence includes the modified Type I IFN-binding protein that does not contain the cell-binding region, but does contain the signal sequence.

pWRG sequence:
SEQ ID NO: 9
GGGGGGGGGGGGCGCTGAGGTCTGCCTCGTGAAGAAGGTGTTGCT

GACTCATACCAGGCCTGAATCGCCCCATCATCCAGCCAGAAAGTG

AGGGAGCCACGGTTGATGAGAGCTTTGTTGTAGGTGGACCAGTTG

GTGATTTTGAACTTTTGCTTTGCCACGGAACGGTCTGCGTTGTCGG

GAAGATGCGTGATCTGATCCTTCAACTCAGCAAAAGTTCGATTTAT

TCAACAAAGCCGCCGTCCCGTCAAGTCAGCGTAATGCTCTGCCAGT

GTTACAACCAATTAACCAATTCTGATTAGAAAAACTCATCGAGCAT

CAAATGAAACTGCAATTTATTCATATCAGGATTATCAATACCATAT

TTTTGAAAAGCCGTTTCTGTAATGAAGGAGAAAACTCACCGAGG

CAGTTCCATAGGATGGCAAGATCCTGGTATCGGTCTGCGATTCCGA

CTCGTCCAACATCAATACAACCTATTAATTTCCCCTCGTCAAAAAT

AAGGTTATCAAGTGAGAAATCACCATGAGTGACGACTGAATCCGG

TGAGAATGGCAAAAGCTTATGCATTTCTTTCCAGACTTGTTCAACA

GGCCAGCCATTACGCTCGTCATCAAAATCACTCGCATCAACCAAAC

CGTTATTCATTCGTGATTGCGCCTGAGCGAGACGAAATACGCGATC

GCTGTTAAAAGGACAATTACAAACAGGAATCGAATGCAACCGGCG

CAGGAACACTGCCAGCGCATCAACAATATTTTCACCTGAATCAGG

ATATTCTTCTAATACCTGGAATGCTGTTTTCCCGGGGATCGCAGTG

GTGAGTAACCATGCATCATCAGGAGTACGGATAAAATGCTTGATG

GTCGGAAGAGGCATAAATTCCGTCAGCCAGTTTAGTCTGACCATCT

CATCTGTAACATCATTGGCAACGCTACCTTTGCCATGTTTCAGAAA

CAACTCTGGCGCATCGGGCTTCCCATACAATCGATAGATTGTCGCA

CCTGATTGCCCGACATTATCGCGAGCCCATTTATACCCATATAAAT

CAGCATCCATGTTGGAATTTAATCGCGGCCTCGAGCAAGACGTTTC

CCGTTGAATATGGCTCATAACACCCCTTGTATTACTGTTTATGTAAG

CAGACAGTTTTATTGTTCATGATGATATATTTTTATCTTGTGCAATG

TAACATCAGAGATTTTGAGACACAACGTGGCTTTCCCCCCCCCCCC

GGCATGCCTGCAGGTCGACATAAATCAATATTGGCTATTGGCCATT

GCATACGTTGTATCTATATCATAATATGTACATTTATATTGGCTCAT

GTCCAATATGACCGCCATGTTGACATTGATTATTGACTAGTTATTA

ATAGTAATCAATTACGGGGTCATTAGTTCATAGCCCATATATGGAG

TTCCGCGTTACATAACTTACGGTAAATGGCCCGCCTCGTGACCGCC

CAACGACCCCCGCCCATTGACGTCAATAATGACGTATGTTCCCATA

GTAACGCCAATAGGGACTTTCCATTGACGTCAATGGGTGGAGTATT

TACGGTAAACTGCCCACTTGGCAGTACATCAAGTGTATCATATGCC

AAGTCCGGCCCCCTATTGACGTCAATGACGGTAAATGGCCCGCCTG

GCATTATGCCCAGTACATGACCTTACGGGACTTTCCTACTTGGCAG

TACATCTACGTATTAGTCATCGCTATTACCATGGTGATGCGGTTTTG

GCAGTACACCAATGGGCGTGGATAGCGGTTTGACTCACGGGGATTT

CCAAGTCTCCACCCCATTGACGTCAATGGGAGTTTGTTTTGGCACC

AAAATCAACGGGACTTTCCAAAATGTCGTAATAACCCCGCCCCGTT

GACGCAAATGGGCGGTAGGCGTGTACGGTGGGAGGTCTATATAAG

CAGAGCTCGTTTAGTGAACCGTCAGATCGCCTGGAGACGCCATCCA

CGCTGTTTTGACCTCCATAGAAGACACCGGGACCGATCCAGCCTCC

GCGGCCGGGAACGGTGCATTGGAACGCGGATTCCCCGTGCCAAGA

GTGACGTAAGTACCGCCTATAGACTCTATAGGCACACCCCTTTGGC

TCTTATGCATGCTATACTGTTTTTGGCTTGGGGCCTATACACCCCCG

CTCCTTATGCTATAGGTGATGGTATAGCTTAGCCTATAGGTGTGGG

TTATTGACCATTATTGACCACTCCCCTATTGGTGACGATACTTTCCA

TTACTAATCCATAACATGGCTCTTTGCCACAACTATCTCTATTGGCT

ATATGCCAATACTCTGTCCTTCAGAGACTGACACGGACTCTGTATT

-continued

```
TTTACAGGATGGGGTCCCATTTATTATTTACAAATTCACATATACA

ACAACGCCGTCCCCCGTGCCCGCAGTTTTTATTAAACATAGCGTGG

GATCTCCACGCGAATCTCGGGTACGTGTTCCGGACATGGGCTCTTC

TCCGGTAGCGGCGGAGCTTCCACATCCGAGCCCTGGTCCCATGCCT

CCAGCGGCTCATGGTCGCTCGGCAGCTCCTTGCTCCTAACAGTGGA

GGCCAGACTTAGGCACAGCACAATGCCCACCACCACCAGTGTGCC

GCACAAGGCCGTGGCGGTAGGGTATGTGTCTGAAAATGAGCTCGG

AGATTGGGCTCGCACCGTGACGCAGATGGAAGACTTAAGGCAGCG

GCAGAAGAAGATGCAGGCAGCTGAGTTGTTGTATTCTGATAAGAG

TCAGAGGTAACTCCCGTTGCGGTGCTGTTAACGGTGGAGGGCAGTG

TAGTCTGAGCAGTACTCGTTGCTGCCGCGCGCGCCACCAGACATAA

TAGCTGACAGACTAACAGACTGTTCCTTTCCATGGGTCTTTTCTGCA

GTCACCGTCCAAGCTTGCGGCCGCGGATCCTCGCAATCCCTAGGAG

GATTAGGCAAGGGCTTGAGCTCACGCTCTTGTGAGGGACAGAAAT

ACAATCAGGGGCAGTATATGAATACTCCATGGAGAAACCCAGATC

TACGTATGATCAGCCTCGACTGTGCCTTCTAGTTGCCAGCCATCTGT

TGTTTGCCCCTCCCCCGTGCCTTCCTTGACCCTGGAAGGTGCCACTC

CCACTGTCCTTTCCTAATAAAATGAGGAAATTGCATCGCATTGTCT

GAGTAGGTGTCATTCTATTCTGGGGGGTGGGGTGGGGCAGGACAG

CAAGGGGGAGGATTGGGAAGACAATAGCAGGCATGCTGGGGATGC

GGTGGGCTCTATGGCTTCTGAGGCGGAAAGAACCAGCTGGGGCTC

GACAGCTCGACTCTAGAATTGCTTCCTCGCTCACTGACTCGCTGCG

CTCGGTCGTTCGGCTGCGGCGAGCGGTATCAGCTCACTCAAAGGCG

GTAATACGGTTATCCACAGAATCAGGGGATAACGCAGGAAAGAAC

ATGTGAGCAAAAGGCCAGCAAAAGGCCAGGAACCGTAAAAAGGC

CGCGTTGCTGGCGTTTTTCCATAGGCTCCGCCCCCCTGACGAGCAT

CACAAAAATCGACGCTCAAGTCAGAGGTGGCGAAACCCGACAGGA

CTATAAAGATACCAGGCGTTTCCCCCTGGAAGCTCCCTCGTGCGCT

CTCCTGTTCCGACCCTGCCGCTTACCGGATACCTGTCCGCCTTTCTC

CCTTCGGGAAGCGTGGCGCTTTCTCAATGCTCACGCTGTAGGTATC

TCAGTTCGGTGTAGGTCGTTCGCTCCAAGCTGGGCTGTGTGCACGA

ACCCCCCGTTCAGCCCGACCGCTGCGCCTTATCCGGTAACTATCGT

CTTGAGTCCAACCCGGTAAGACACGACTTATCGCCACTGGCAGCA

GCCACTGGTAACAGGATTAGCAGAGCGAGGTATGTAGGCGGTGCT

ACAGAGTTCTTGAAGTGGTGGCCTAACTACGGCTACACTAGAAGG

ACAGTATTTGGTATCTGCGCTCTGCTGAAGCCAGTTACCTTCGGAA

AAAGAGTTGGTAGCTCTTGATCCGGCAAACAAACCACCGCTGGTA

GCGGTGGTTTTTTTGTTTGCAAGCAGCAGATTACGCGCAGAAAAA

AGGATCTCAAGAAGATCCTTTGATCTTTTCTACGGGTCTGACGCT

CAGTGGAACGAAAACTCACGTTAAGGGATTTTGGTCATGAGATTAT
```

```
CAAAAAGGATCTTCACCTAGATCCTTTTAAATTAAAAATGAAGTTT

TAAATCAATCTAAAGTATATATGAGTAAACTTGGTCTGACAGTTAC

CAATGCTTAATCAGTGAGGCACCTATCTCAGCGATCTGTCTATTTC

GTTCATCCATAGTTGCCTGACTC
```

In a further embodiment, the present invention relates to host cells stably transformed or transfected with the above-described recombinant DNA constructs. The host cell can be prokaryotic such as *Bacillus* or *E. coli*, or eukaryotic such a *Saccharomyces* or *Pichia*, or mammalian cells or insect cells. The vector containing the DNA sequence of the modified IFN-binding protein is expressed in the bacteria and the expressed product used for any of the purposes described herein. Please see e.g., Maniatis et al., 1985 Molecular Cloning: A Laboratory Manual or DNA Cloning, Vol. I and II (D. N. Glover, ed., 1985) for general cloning methods. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the modified IFN-binding protein DNA sequences are operably linked to a promoter which can be expressed in the transfected cell.

DESCRIPTION OF THE FIGURES

FIG. 1A) Schematic depicting C-terminal truncation mutants. FIG. 1B) The ability of the C-terminal mutants to bind and neutralize Type I IFNs was examined. Plasmids encoding each molecule were transfected into COS-7 cells using fugene6. 48 hour post-transfection, medium from cell cultures was collected and clarified by low speed centrifugation. Clarified medium was added to a Type I IFN signaling cells line, 293:IFN cell and incubated for 2 hours with rocking every 15 minutes. After incubation, cells were washed twice with PBS and medium containing Type I IFN-alpha (500 U/ml) was added back to certain wells. Cells were incubated overnight (24 hours) at 37 degree Celsius in the presence of 5% CO2. After 24 hours, cells were removed from plates by gentle agitation and washed in FACS buffer followed by low speed centrifugation. Cells were then resuspended in PBS (1×10(6) cells/ml) and analyzed on a flow cytometer for RFP expression. Legend: Cells incubated with medium alone and without IFN-alpha (grey area), the C-terminal mutant 700 (red line), the C-terminal mutant 400 (yellow line) the full length IMB containing medium (blue area) or media alone plus IFN-alpha (black line).

FIG. 2A) Schematic depicting N-terminal truncation mutants. FIG. 2B) The ability of the IBM and N-terminal mutants to neutralize Type I IFNs was investigated. Plasmids encoding each molecule were transfected into COS-7 cells using fugene6. 48 hour post-transfection, medium from cell cultures was collected and clarified by low speed centrifugation. Clarified medium was added to a Type I IFN signaling cells line, 293:IFN cell, which contain a red fluorescent protein under the control of an Type I inducible promoter. Cell monolayers were incubated for 2 hours with rocking every 15 minutes. After incubation, cells were washed twice with PBS and medium containing Type I IFN-alpha (500 U/ml) was added back to the wells. Cells were incubated overnight (24 hours) at 37 degree Celsius in the presence of 5% CO2. After 24 hours, cells were removed from plates by gentle agitation and washed in FACS buffer followed by low speed centrifugation. Cells were then resuspendend in PBS (1×10(6) cells/ml) and analyzed on a flow cytometer for RFP expression. Cells incubated with medium alone (grey area) (positive IFN-signaling control), cells incubated with N-terminal mutant 7 (grey line), cells incubated with N-terminal mutant 4 (black line) and cells incubated with IBM containing medium (black area).

FIG. 4 shows how the therapeutic compositions would be used to neutralize Type I interferon to treat systemic inflammatory response syndrome (e.g., sepsis, viral hemorrhagic fever). This is contrast to the full-length B19 IFN-binding protein, which would not permit systemic spread of the protein because the cell-binding protein causes the entire B19 protein to bind to cells. Therefore the B19 would not effectively neutralize IFNs, whereas the therapeutic compositions would.

FIG. 5A and FIG. 5B show neutralization using modified IFN-binding protein (without cell-binding region and without signal sequence) which as expressed with an *E. coli* expression system, specifically a pET vector system that uses a T7 polymerase to drive expression of the DNA sequence of interest. It is a commercially available system. As shown by these results, this embodiment of the modified IFN-binding protein does neutralize IFN, just 10-fold or greater less-efficiently than when expressed in mammalian cells. This is consistent with what we believe would be true from expression in insect cells. Earlier studies showed that with the full-length molecule, bacteria and yeast produced a molecule with decreased efficacy.

FIG. 6A) At −24 h, three groups of 8 mice/group where injected with 2 ml of medium containing B19, INP (700) or medium from control cells. As a positive control 8 animals were injected with a single 1 mg i.p. injection of MAR1-5A3, an anti-IFN receptor antibody. At 0 h, mice were given another i.p. dose of 2 ml B19, 700 or medium alone. Medium for all groups also contained 30 ug of murine TNF-alpha. Survival was monitored for 72 h after TNF-alpha was given. FIG. 6B) Panel B shows a survival curve of treated mice. Significant protection was afforded to groups receiving B19 and the truncated version of the molecule (700). Over half of the animals in these two groups survived challenge.

Figure 6A:
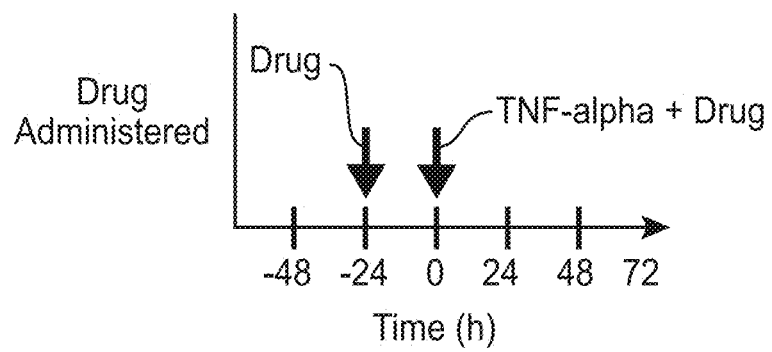
FIG. 6A and FIG. 6B show that B19 and INP(700) [interferon neutralizing protein designated in figure as INP] protect mice against TNF-alpha induced shock.
Figure 6B:
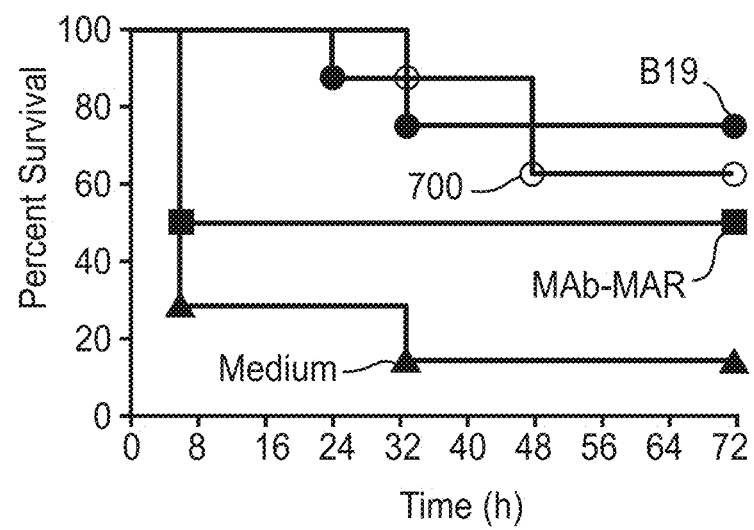

Conclusion for FIG. 6A and FIG. 6B: These findings show that B19 or INP can protect mice from the lethal effects of TNF-alpha induced shock. Protective efficacy was better than an antibody (MAb-MAR) that binds to the type I IFN receptor molecule and blocks IFN signaling. This is the first in vivo evidence that the orthopoxvirus molecule B19 or our truncated version of the molecule can protect against lethal shock in mice.

DETAILED DESCRIPTION OF PREFERRED EMBODIMENTS

Orthopoxviruses encode a Type I IFN-binding protein (IBP)—sometimes referred to as the IFN binding molecule or IBM—of which the Vaccinia virus ortholog is called B18R or B19R depending on the strain of Vaccinia virus. This molecule is secreted from infected cells whereupon it can interact and block Type I IFN activity (1, 2, 12). However, a unique capability of the orthopoxviruses IBM is its ability to bind to the cell surface of uninfected cells surrounding the infected cells to prevent the development of an Type I IFN induced antiviral state in the uninfected cells (2). In doing so, this molecule helps the virus spread to nearby cells, where it replicates and spreads to respective nearby cells—thus enabling viral dissemination. This molecule can be critically important for some orthopoxviruses infections, for example it is essential for infection by Ectromelia virus infection (the orthologs of Vaccinia IBM is called ECV166) and vaccines targeting this molecule are 100% protective (14).

The full-length poxvirus IFN-binding protein is sold as a research reagent. To investigate the IFN-binding protein as a vaccine target, the separate domains involved in IFN neutralization and cell binding have been identified in Golden and Hooper, 2010 (Clinical and Vaccine Immunology, 2010, vol. 17, no. 11, p. 1656-1665). It was found that the Type I IFN-neutralizing region and the cell-binding region maintain respective activity independent of each other. We theorized that the IFN-binding domain/region would be an effective component in a vaccine against Vaccinia virus (and its orthologs). The IFN-binding domain is touted for its capacity to neutralize Type I IFNs at the cell-surface and in the extracellular milieu ((4) and also for example see ebioscience catalogue #34-8185 B18R full-length protein-"unique in that it exists as a soluble extracellular, as well as cell-surface protein, enabling blockage of both autocrine and paracrine IFN functions"). We thought that as a vaccine target, targeting the CBP or the IFN-neutralization regions may enhance the vaccine targeting of the molecule by focusing the immune response onto those domains.

Figure 1A:
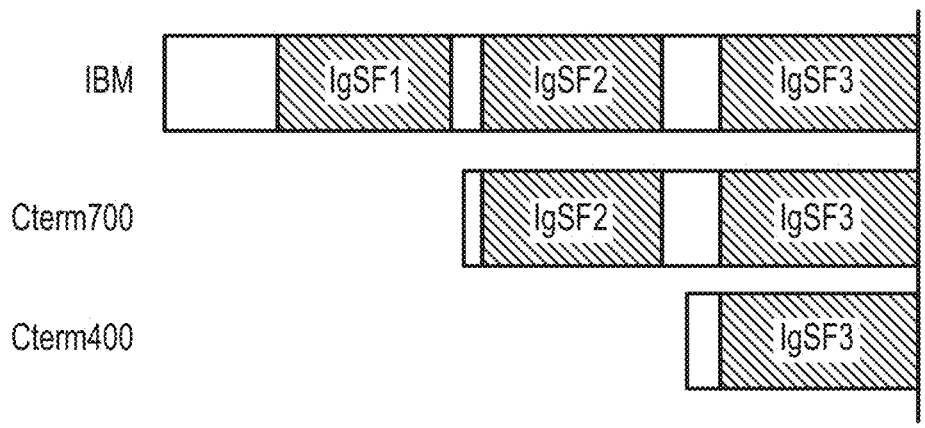
FIG. 1A and FIG. 1B show the isolation of the Type I IFN binding region of the poxvirus IBM.
Figure 1B:
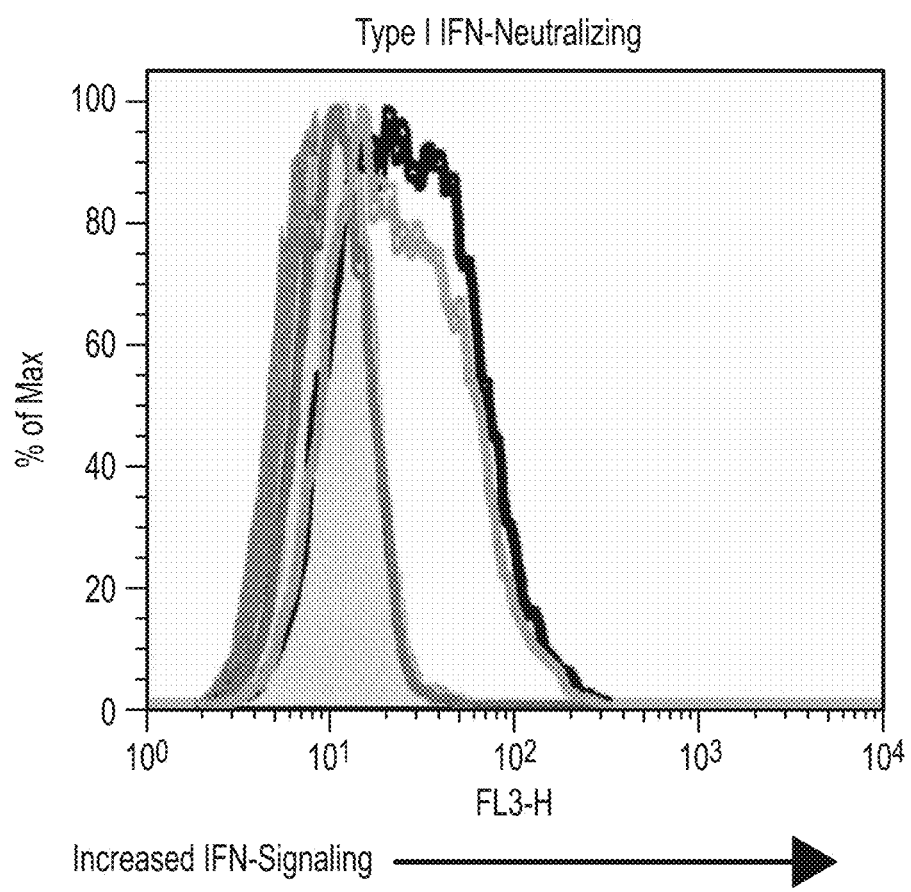
Figure 2A:
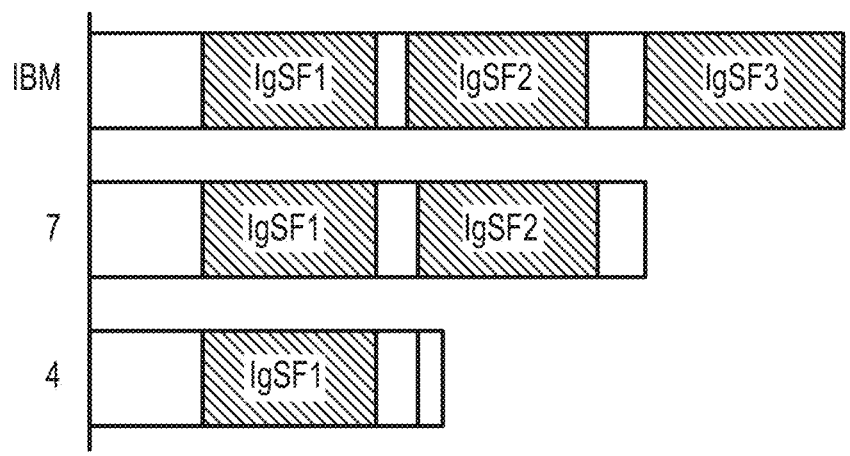
FIG. 2A and FIG. 2B show the isolation of the cell-binding region of the orthopoxvirus Type I IFN binding molecule (B19R/B18R/VACVWR200).
Figure 2B:
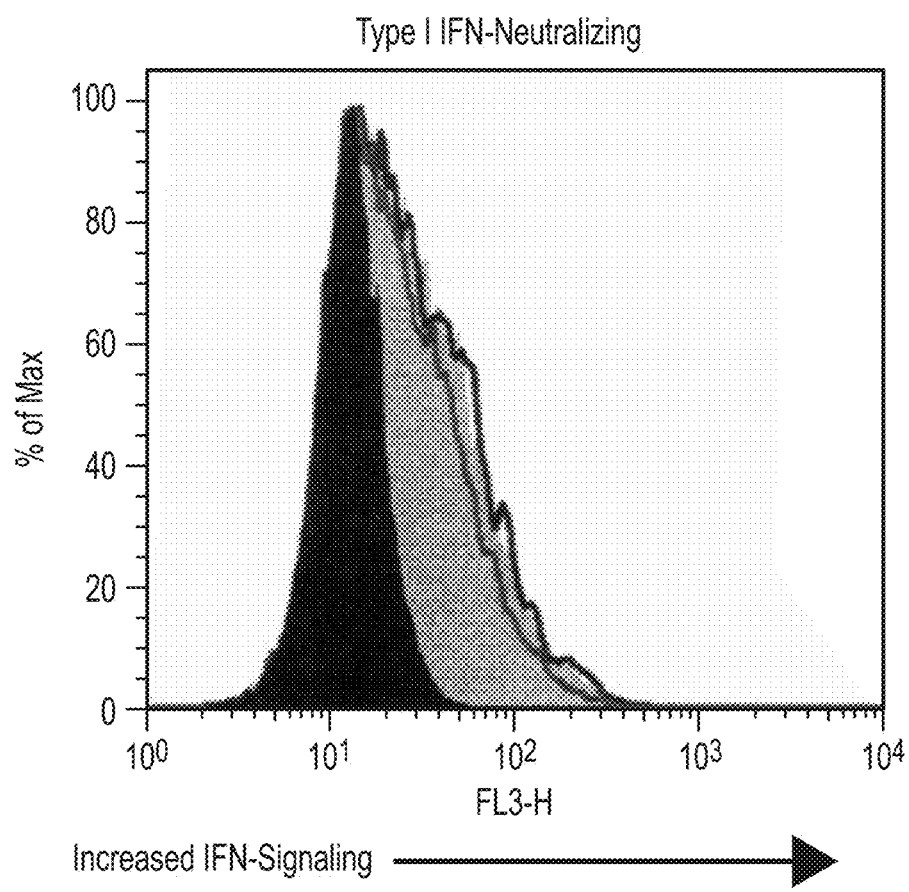
Figure 3:
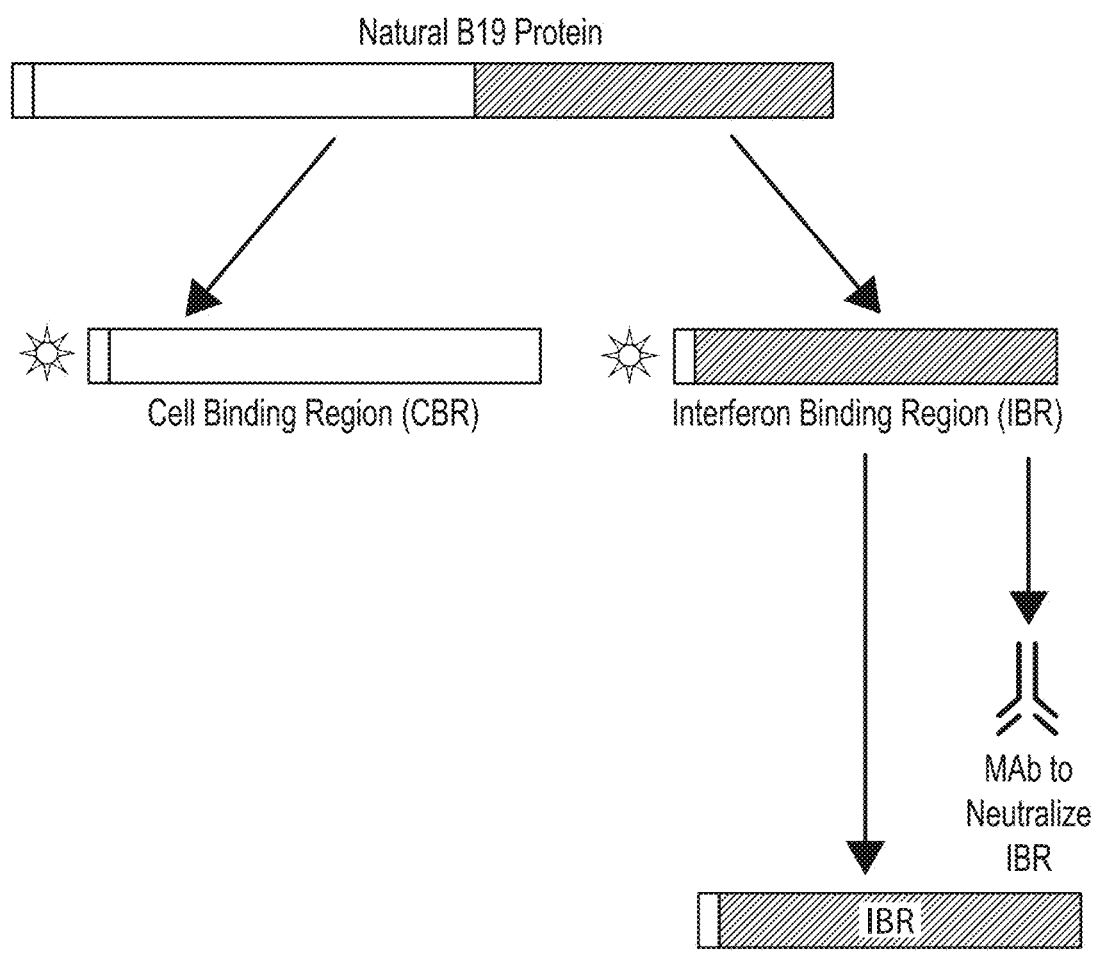
FIG. 3 shows the cellular binding and Type I IFN binding regions of the Orthopoxvirus Type I interferon binding molecule.

What we found, however, was that vaccines containing the IFN-binding region and targeting the Vaccinia virus ortholog IBM (B18R/B19R) failed to protect animals from lethal Vaccinia virus infection. This was true even though the molecules are immunogenic and generate antibodies that neutralize IFN function. Further, the level of the immune response did not seem to inhibit the function of the IBM as it still was able to neutralize Type I IFN in the presence of serum antibodies produced in the vaccinate animals, but to a slightly reduced level. However, when B18/B19 was combined with other targets there was some improvement in the combination vaccine (see Ref. 15, FIG. 2) in terms of weight loss and survival in vaccinated and virus challenge animals. Given that we saw limited improvement in our vaccine when this molecule was included, its usefulness as a vaccine target to protect against human pathogenic poxviruses is doubtful.

Subsequent to those experiments and results, we pursued a completely different route—therapeutic compositions and uses. We found, unexpectedly, that in vivo experiments showed successful therapeutic use in mice (data below). We postulate that this is because the immune response against did not completely disrupt function of our modified IFN-binding protein, and our protein was not itself targeted by the immune response by antibodies—although it turned out to be a poor antigen (for vaccine use). In our earlier paper (Golden and Hooper, 2010, Clinical and Vaccine Immunology), the data show that antibodies targeting the molecule impact the neutralizing ability of the molecule. However, subsequently we tested our modified IFN-binding protein in vivo as a therapeutic and discovered that it protected mice in a model of shock.

We did not expect the modified IFN-binding region to spread systemically, we only expected it would create an immune response that would not only target the molecule but prevent the virus from infecting. That immune response would be reasonably expected to target this viral effector molecule in a way that prevented its function, in addition to potentially targeting infected cells expressing this molecule.

We theorized that the cell-binding domain was actually a hindrance to the power of this broadly neutralizing molecule. If a therapeutic composition had a cell-binding domain, which the IFN-binding protein naturally does, those skilled in the art would understand that the ability of the molecule to diffuse systemically when injected into a host would be limited.

Figure 4:
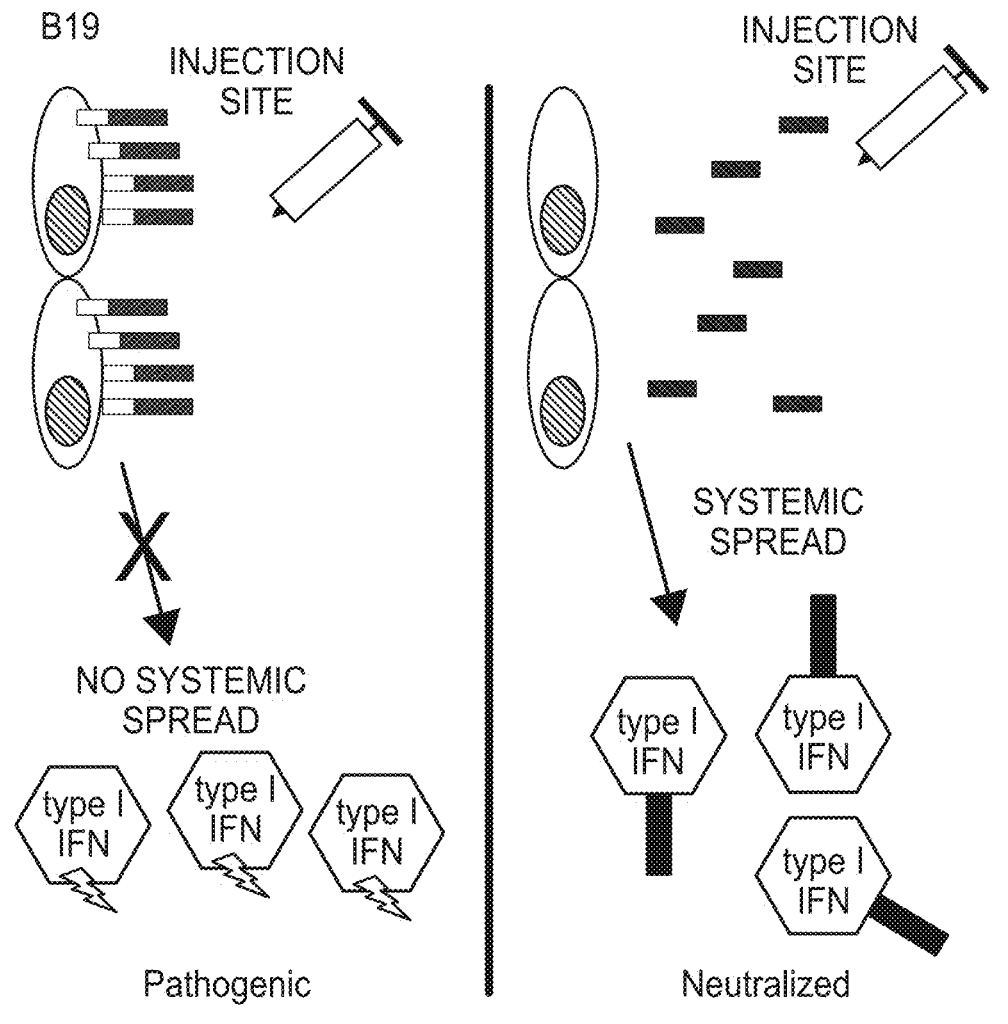

When we removed the cell binding region in the orthopoxvirus (Vaccinia B19) IFN-binding protein, we discovered unexpectedly that this creates a fully soluble (in cell tissues and matrices) peptide molecule having potent cap ability to bind to and neutralize Type 1 IFN-alpha and -beta, and presumably -kappa and -epsilon, from multiple species including humans. To our knowledge, this is a novel broad spectrum drug to prevent pathology caused by the activity of IFN. It is therapeutically useful to reduce and neutralize Type I IFN in a subject or patient, or otherwise block the IFNs in vitro and in vivo (see FIGS. 4 and 6A and B). In addition, the use of a viral protein, rather than a human protein, is advantageous because there is less chance of inducing auto-immunity.

Type I IFNs are critical in the daily defense of the host from a variety of insults, including infectious disease. The use of type I IFN targeting molecules that are derived from the host (i.e. receptors) is the possibility that antibodies targeting these molecules will be produced in the host during treatment. These auto-antibodies may disrupt natural signaling in the host and cause them to be more susceptible to infection due to a dis-regulated Type I IFN response.

Because Type I IFN is involved in systemic inflammatory response syndrome (SIRS), one utility of this molecule is to inject it into a host whereby it will diffuse systemically (as it lacks the cell binding domain). It would then neutralize Type I IFN and reduce the pathology associated with SIRS. One embodiment of the invention, therefore, is a method to treat or alleviate the symptoms of SIRS. (See FIG. 4, where following injection of the therapeutic composition into a host, the composition will diffuse systemically.)

Recent studies indicate the neutralization of Type I IFN in the treatment of various disorders, including sepsis and viral hemorrhagic fevers, might be an effective means of abating their pathology. Molecules that can broadly neutralize many Type I IFNs, as opposed to just IFN-a or IFN-b subclasses, would be very useful. Our invention has the capacity to bind both Type I IFN classes (alpha and beta). Furthermore, our molecule binds Type I IFNs from a wide variety of species making it useful in treatment of human and animal diseases. The invention can be used in broad spectrum drugs, as a medicament for treating or preventing a number of disorders or syndromes. One example is sepsis, and other systemic inflammatory disorders and as a therapeutic to treat inflammatory disorders caused by, or perpetuated by, IFNa/b (e.g., lupus, and other autoimmune diseases). Our compositions are useful to neutralize the over-production of interferon, and relieve symptoms. Essentially any malady that is exacerbated by over-production of interferon could be targeted by our modified IFN-binding protein.

Other examples of the types of medical conditions or issues that are caused by, or exacerbated by, increased Type I IFN (inflammation), our therapeutic compositions may be useful to treat include: cardiovascular disease, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, hypercoagulation, hemophilia, ulcers, wounds, lesions, cuts, abrasions, oxidative damage, age-related tissue degeneration, surgically related lesions, burns, muscle weakness, muscle atrophy, connective tissue disorders, idiopathic thrombocytopenic purpura, heart failure, secondary pathologies caused by heart failure and hypertension, hypotension, angina pectoris, myocardial infarction, tuberous sclerosis, scleroderma, transplantation, inflammation, chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.) Hyperproliferative Disorders, neoplasms, autoimmune disease, cystic fibrosis, allergic reactions and conditions, such as asthma (particularly allergic asthma) or other respiratory problems, hemolytic anemia, antiphospholipid syndrome, rheumatoid arthritis, dermatitis, allergic encephalomyelitis, glomerulonephritis, Goodpasture's Syndrome, Graves'Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Autoimmune Pulmonary Inflammation, Guillain-Barre Syndrome, insulin dependent diabetes mellitus, and autoimmune inflammatory eye disease, naphylaxis, hypersensitivity to an antigenic molecule, or blood group incompatibility, graft versus host disease (GVHD), lupus erythematosus, viral/bacterial/parasitic infections, multiple sclerosis, autoimmune disease, allergies, immunodeficiencies, graft versus host disease, asthma, emphysema, ARDS, inflammation and modulation of the immune response, viral pathogenesis, aging-related disorders, Th1 inflammatory diseases such as rheumatoid arthritis, multiple sclerosis, inflammatory bowel diseases, AIDS, wound repair, heart attacks, heart failure, muscular dystrophy, bed sores, diabetic ulcers, oxidative damage, and tissue damage such as sinusitis or mucositis, wrinkles, eczema or dermatitis, dry skin, obesity, diabetes, endocrine disorders, anorexia, bulimia, renal artery stenosis, interstitial nephritis, glomerulonephritis, polycystic kidney disease, systemic, renal tubular acidosis, IgA nephropathy, nephrological disesases, hypercalceimia, Lesch-Nyhan syndrome, Von Hippel-Lindau (VHL) syndrome, trauma, regeneration (in vitro and in vivo), Hirschsprung's disease, Crohn's Disease, appendicitis, endometriosis, laryngitis, psoriasis, actinic keratosis, acne, hair growth/loss, allopecia, pigmentation disorders, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, muscle disorders, urinary retention, Albright Hereditary Ostoeodystrophy, ulcers, Alzheimer's disease, stroke, Parkinson's disease, Huntington's disease, cerebral palsy, epilepsy, Lesch-Nyhan syndrome, multiple sclerosis, ataxia-telangiectasia, behavioral disorders, addiction, anxiety, pain, neuroprotection, Stroke, Aphakia, neurodegenerative disorders, neurologic disorders, developmental defects, conditions associated with the role of GRK2 in brain and in the regulation of chemokine receptors, encephalomyelitis, anxiety, schizophrenia, manic depression, delirium, dementia, severe mental retardation and dyskinesias, Gilles de la Tourette syndrome, leukodystrophies, cancers, breast cancer, CNS cancer, colon cancer, gastric cancer, lung cancer, melanoma, ovarian cancer, pancreatic cancer, kidney cancer, colon cancer, prostate cancer, neuroblastoma, and cervical cancer, Neoplasm; adenocarcinoma, lymphoma; uterus cancer, benign prostatic hypertrophy, fertility, control of growth and development/differentiation related functions such as but not limited maturation, lactation and puberty, reproductive malfunction, and/or other pathologies and disorders of the like.

Other investigators have used human interferons as drugs and candidate drugs. To our knowledge, though, proteins or peptides that bind to and neutralize interferons have not been developed as drugs, especially therapeutic drugs.

In another embodiment, the therapeutic compositions could be used for animal model development. The soluble modified IFN-binding protein can be used to create transient interferon alpha/beta deficient animals. Treated animals would be susceptible to viruses and other pathogens that must circumvent the innate immune response (e.g., Type 1 interferon) to establish infection and cause disease.

In another embodiment, a monoclonal antibody would be produced to inactivate and remove the soluble modified IFN-binding protein. This antibody could be used in combination with the modified protein as a means for clinicians to regulate levels of active IFN.

Figure 5A:
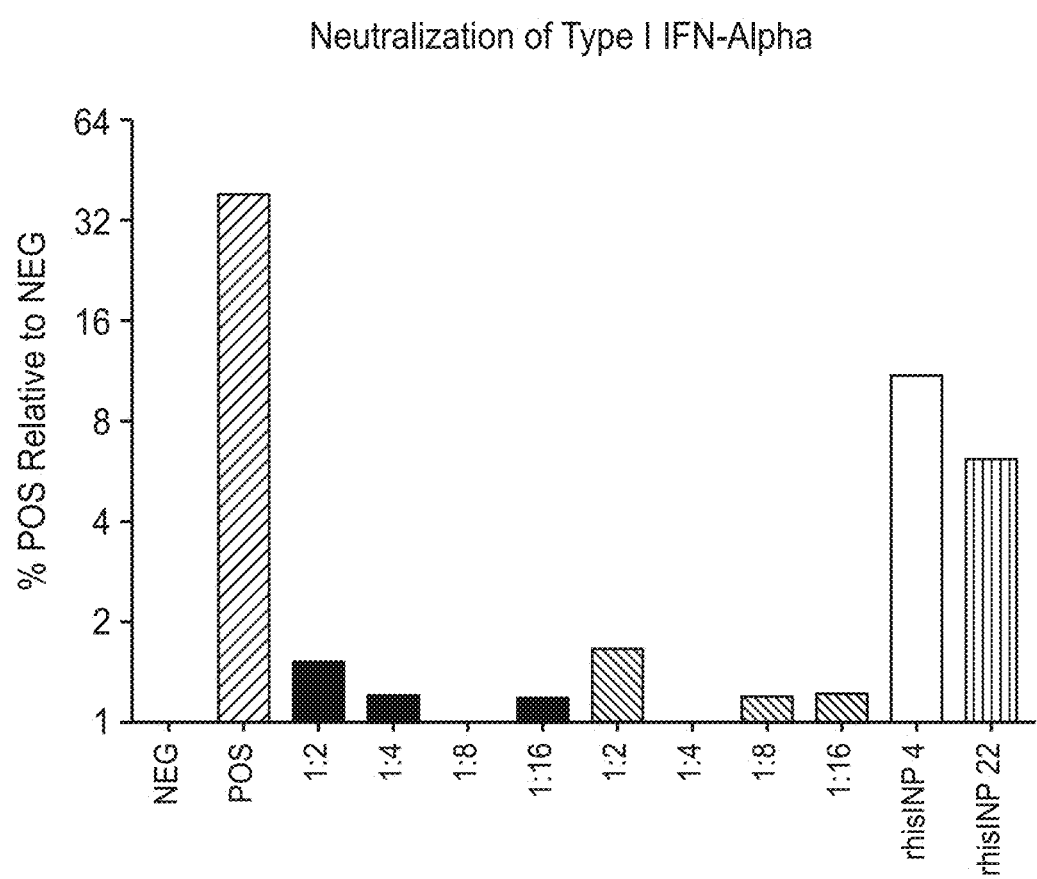
FIG. 5A and FIG. 5B show the neutralization of Type 1 IFN alpha and beta by B19 (full length protein) and the interferon neutralizing protein (designated in figure as INP). B19 or INP was produced by transfecting 293 cells with plasmids encoding each molecule. After three days, medium was removed and clarified by low speed centrifugation. Subsequently, media containing the expressed proteins at the indicated dilutions were incubated in total volume of 1 ml of medium containing recombinant human IFN-alpha (250 units) or human IFN-beta (150 units) for 3 hours at 37 degrees Celsius. A negative control consisted of medium without IFN (lowest value) and the positive control consisted of IFN in medium without B19 or INP (highest value). Medium was added to monolayers of 293:IFN cells, which produce a detectable red fluorescence signal when exposed to human Type I IFNs and incubated for 20-24 hours at 37 degrees Celsius. After incubation, cells were analyzed by flow cytometry for expression of red fluorescent protection. Percent positive cells were calculated based on the signal produced by the negative control. In this experiment, we also included bacterially expressed INP, which was his-tagged. (Histidine tags allow purification of bacterially expressed proteins using nickel columns.) Protein samples (80 micrograms/ml) were incubated with medium containing IFN as above. Protein was purified on his columns under reducing conditions (8M urea) and refolded by dilatation against PBS either at 4 degrees Celsius or 22 degrees Celsius. Protein purified at 22 degrees Celsius was slightly more reactive. However, overall his-tagged protein was less efficacious than cell-culture derived untagged molecule. These findings show that cell culture produced B19 or INP is potent even when diluted (data not shown). Other studies have shown that dilution of 1:400 yields more than 80% or more than 50% neutralization of IFN-alpha and IFN-beta, respectively.
Figure 5B:
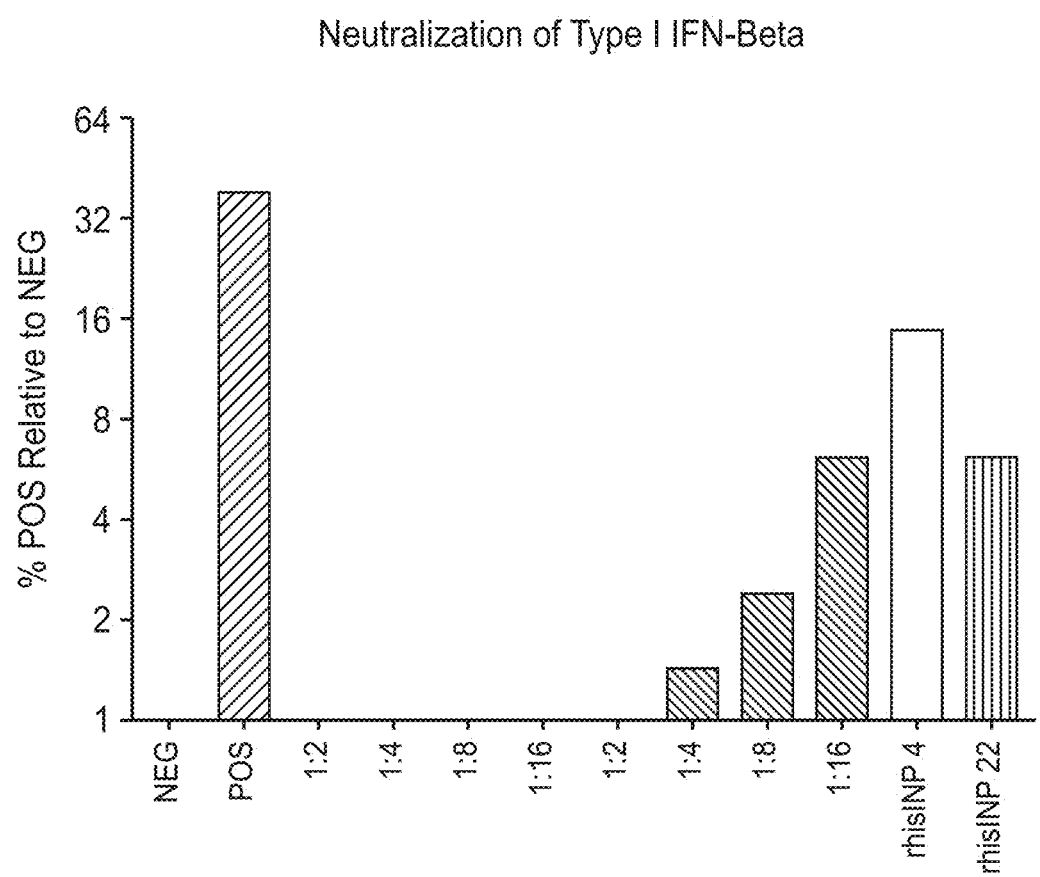

In a different embodiment, we have a different composition of the modified IFN-binding protein. As described above, this modified protein has neither the cell-binding region nor the signal sequence—it only contains the interferon binding region (IBR; or interferon binding region). Preferably, this embodiment of the modified IFN-binding protein has the amino acid sequence of SEQ ID NO:2, which corresponds to the IBR in the Vaccinia virus B19 protein. This modified IFN-binding protein without the signal sequence, when expressed in E. coli, resulted in a weaker binding of Type I IFN than the embodiment containing the signal sequence—e.g., about 10-fold less. FIG. 5A and FIG. 5B show bacterial expression of the modified IFN-binding region of this embodiment. However, this molecule has the advantageous capacity to be expressed in a variety of expression systems—e.g., bacterial (such as E. coli), insect, yeast, and mammalian cells. As shown, expression was less than a mammalian expression system, but still produced enough to generate sufficient quantities of modified IFN-binding protein to be useful for many applications. Expressing this modified IFN-binding protein in an E. coli expression system resulted in a product that is not as specifically binding as the IBR with the signal sequence expressed in mammalian cells, but is effective in binding IFNs in a mammalian subject. Because of the efficiency of protein expression in E. coli, the decrease in efficacy we observed may be overshadowed by the ability to produce a lot of protein. This may mean that more recombinant protein expressed from E. coli would be required for treatment, but there are potential advantages of using such a non-mammalian expression system, including cost savings.

In a preferred embodiment, the modified IFN-binding protein has the following sequence, which does not contain the cell-binding region but does contain the signal sequence. This is designated as SEQUENCE ID NO:1.

```
Amino acids 1-52; 148-351
(note 1-52 contains the predicted secretion
signal and not IFN-binding region)
                              (SEQUENCE ID NO: 1)
MTMKMMVHIYFVSLLLLLFHSYAIDIENEITEFFNKMRDTLPAKDS

KWLNPAPPSCIPKTYELGTHDKYGIDLYCGILYAKHYNNITWYKDN

KEINIDDIKYSQTGKELIIHNPELEDSGRYDCYVHYDDVRIKNDIV

VSRCKILTVIPSQDHRFKLILDPKINVTIGEPANITCTAVSTSLLI

DDVLIEWENPSGWLIGFDFDVYSVLTSRGGITEATLYFENVTEEYI

GNTYKCRGHNYYFEKTLTTTVVLE
```

In another embodiment, the modified IFN-binding protein has the following sequence of the Vaccinia virus B19 IFN-binding protein, which contains neither the cell-binding region nor the signal sequence. This is designated as SEQUENCE ID NO:2.

(SEQUENCE ID NO:2) a M was added to the start and is the requisite start codon, the raw sequence starts with the P.

```
MPPSCIPKTYELGTHDKYGIDLYCGILYAKHYNNITWYKDNKEINI

DDIKYSQTGKELIIHNPELEDSGRYDCYVHYDDVRIKNDIVVSRCK

ILTVIPSQDHRFKLILDPKINVTIGEPANITCTAVSTSLLIDDVLI

EWENPSGWLIGFDFDVYSVLTSRGGITEATLYFENVTEEYIGNTYK

CRGHNYYFEKTLTTTVVLE
```

The following is the amino acid sequence for the signal sequence of the Vaccinia virus B19 IFN-binding protein. This is designated as SEQUENCE ID NO:3.

```
                                      (SEQUENCE ID NO: 3)
MTMKMMVHIYFVSLLLLLFHSYAIDIENEITEFFNKMRDTLPAKDS
KWLNPA
```

The following is the DNA sequence for the modified IFN-binding protein of the Vaccinia virus B19 IFN-binding protein, which does not contain the cell-binding region but does contain the signal sequence. The initial ATG is the start codon. This encodes SEQUENCE ID NO:1. This is designated as SEQUENCE ID NO:4.

```
Type I IFN binding region
1-156; 448-1053 (codon optimized)
                                      (SEQUENCE ID NO: 4)
ATGACCATGAAGATGATGGTGCACATCTACTTCGTGAGCCTGCTG

TCCTGCTGTTCCACAGCTACGCCATCGACATCGAGAACGAGATCAC

CGAGTTCTTCAACAAGATGCGGGACACCCTGCCCGCCAAGGACAG

CAAGTGGCTGAACCCCGCCCCCCCCAGCTGCATCCCCAAGACCTAC

GAGCTGGGCACCCACGACAAGTACGGCATCGACCTGTACTGCGGC

ATCCTGTACGCCAAGCACTACAACAACATCACCTGGTATAAGGAC

AACAAAGAGATCAACATCGACGACATCAAGTACAGCCAGACCGGC

AAAGAGCTGATCATCCACAACCCCGAGCTGGAAGATAGCGGCAGA

TACGACTGCTACGTGCACTACGACGACGTGCGGATCAAGAACGAC

ATCGTGGTGTCCCGGTGCAAGATCCTGACCGTGATCCCCAGCCAGG

ACCACCGGTTCAAGCTGATCCTGGACCCCAAGATCAACGTGACCAT

CGGCGAGCCCGCCAATATCACCTGCACCGCCGTGAGCACCAGCCT

GCTGATCGACGATGTGCTGATCGAGTGGGAGAACCCTAGCGGCTG

GCTGATCGGCTTCGACTTCGACGTGTACAGCGTGCTGACCAGCAGG

GGCGGCATCACCGAGGCCACCCTGTACTTCGAGAACGTGACCGAG

GAATACATCGGCAACACCTACAAGTGCAGGGGCCACAACTACTAC

TTCGAAAAGACCCTGACCACCACCGTGGTGCTGGAA
```

The following is the DNA sequence for the modified IFN-binding protein of the Vaccinia virus B19 IFN-binding protein, which contains neither the cell-binding region nor the signal sequence. This encodes SEQUENCE ID NO:2. This is designated as SEQUENCE ID NO:5. (The ATG is the start codon needed for expression)

```
                                      (SEQUENCE ID NO: 5)
ATGCCCCCCAGCTGCATCCCCAAGACCTACGAGCTGGGCAC

CCACGACAAGTACGGCATCGACCTGTACTGCGGCATCCTGTACGCC

AAGCACTACAACAACATCACCTGGTATAAGGACAACAAAGAGATC

AACATCGACGACATCAAGTACAGCCAGACCGGCAAAGAGCTGATC

ATCCACAACCCCGAGCTGGAAGATAGCGGCAGATACGACTGCTAC

GTGCACTACGACGACGTGCGGATCAAGAACGACATCGTGGTGTCC

CGGTGCAAGATCCTGACCGTGATCCCCAGCCAGGACCACCGGTTC

AAGCTGATCCTGGACCCCAAGATCAACGTGACCATCGGCGAGCCC

GCCAATATCACCTGCACCGCCGTGAGCACCAGCCTGCTGATCGACG

ATGTGCTGATCGAGTGGGAGAACCCTAGCGGCTGGCTGATCGGCTT

CGACTTCGACGTGTACAGCGTGCTGACCAGCAGGGGCGGCATCAC

CGAGGCCACCCTGTACTTCGAGAACGTGACCGAGGAATACATCGG

CAACACCTACAAGTGCAGGGGCCACAACTACTACTTCGAAAAGAC

CCTGACCACCACCGTGGTGCTGGAA
```

The following is the DNA sequence for the signal sequence of the Vaccinia virus B19 IFN-binding protein. The initial ATG is the start codon. This encodes SEQUENCE ID NO:3. This is designated as SEQUENCE ID NO:6.

```
                                      (SEQUENCE ID NO: 6)
ATGACCATGAAGATGATGGTGCACATCTACTTCGTGAGCCT

GCTGCTCCTGCTGTTCCACAGCTACGCCATCGACATCGAGAACGAG

ATCACCGAGTTCTTCAACAAGATGCGGGACACCCTGCCCGCCAAG

GACAGCAAGTGGCTGAACCCCGCC
```

The following is the DNA sequence for the cell binding region of the Vaccinia virus B19 IFN-binding protein. The initial ATG is the start codon. This contains the secretion signal sequence.

```
Cell binding region
1-486 (codon optimized for expression)
(signal sequence = 1-156)
                                      (SEQUENCE ID NO: 7)
ATGACCATGAAGATGATGGTGCACATCTACTTCGTGAGCCTGCTGC

TCCTGCTGTTCCACAGCTACGCCATCGACATCGAGAACGAGATCAC

CGAGTTCTTCAACAAGATGCGGGACACCCTGCCCGCCAAGGACAG

CAAGTGGCTGAACCCCGCCTGCATGTTCGGCGGCACCATGAACGA

TATCGCCGCCCTGGGCGAGCCCTTCAGCGCCAAGTGCCCCCCCATC

GAGGACAGCCTGCTGTCCCACCGGTACAAGGACTACGTGGTGAAG

TGGGAGCGGCTGGAAAAGAACCGGCGGAGGCAGGTGTCCAACAA

GAGAGTGAAGCACGGCGACCTGTGGATCGCCAACTACACCAGCAA

GTTCAGCAACCGGCGCTACCTGTGCACCGTGACCACCAAGAACGG

CGACTGCGTGCAGGGCATCGTGCGGAGCCACATCCGGAAGCCCCC

CAGCTGCATCCCCAAGACCTACGAGCTGGGCACC
```

The following is the amino acid sequence for the cell binding region of the Vaccinia virus B19 IFN-binding protein, also including the signal sequence at positions 1-52.

```
B19 1-162 (Amino acids)
                                      (SEQUENCE ID NO: 8)
MTMKMMVHIYFVSLLLLLFHSYAIDIENEITEFFNKMRDTLPAKDS

KWLNPACMFGGTMNDIAALGEPFSAKCPPIEDSLLSHRYKDYVVKW

ERLEKNRRRQVSNKRVKHGDLWIANYTSKFSNRRYLCTVTTKNGDC

VQGIVRSHIRKPPSCIPKTYELGT
```

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

Results—Advantages and Unexpected Results

We hypothesized that removal of the cell-binding region of the IBM (interferon binding molecule, or interferon binding protein) would generate a novel molecule lacking cell binding function, but retaining the capacity to bind Type I IFNs. The pragmatic value of this modification is that the molecule would be better suited for diffusion within a host upon injection, as in its natural context, the cell-binding domain would limit dissemination through the host because the molecule would bind cells near the injection site.

TNF-alpha is a potent mediator of inflammation and recent reports have indicated that this cytokine induces SIRS in a Type I IFN-dependent fashion (11). In FIGS. 6A and B, we used a TNF-alpha toxemia mouse model to determine if neutralizing of type I IFN using B19 and the modified B19 without the cell-binding region had a positive impact on animals treated with an otherwise lethal dose of that cytokine. In this model, injection of TNF-alpha causes SIRS and unprotected mice succumb rapidly. Mice unable to utilize Type I IFN due to genetic mutation (Type I IFN receptor knockout or IFN-beta knockout) do not succumb to treatment (11). By using the orthopoxvirues type IFN neutralizing molecules, we hypothesized that similar to knockout mice, B19-treated animals will produce significantly lower levels of cytokines and have a better survival curve versus mice treated with the negative control. At –24 h, three groups of 10 mice/group were injected by the intraperitoneal route with 2 ml of mammalian cell culture medium containing B19, the B19 molecule without the cell-binding domain (700), an antibody MAb-MAR that blocks the type I IFN receptor or the negative control consisting of cell culture medium without any additives. At 0 h, mice were administered another i.p. dose of type I IFN-neutralizing molecules in a bolus that also contained 30 micrograms of murine TNF-alpha. As shown in FIGS. 6A and B, control mice rapidly succumbed to TNF-alpha and by 8h these mice were dead. In addition, half of the mice receiving a signal dose of the MAb-MAR had to be euthanized due to severe inflammation. In marked contrast, mice receiving either B19 or the B19 without the cell-binding region did not begin to succumb to inflammation until 24 h after challenge. In addition, over half the mice in each group survived challenge with TNF-alpha up to 72 h, the time at which all remaining mice where euthanized. This experiment provides the first proof-of-concept data indicating the B19 molecule and the non-cell binding version of this molecule (700) are effective in combating SIRS mediated by TNF-alpha. It suggests this molecule will have therapeutic value (anti-type I IFN) despite our interest in making it a vaccine target.

A modified IFN-binding protein lacking the signal sequence and the cell-binding domain was synthesized de novo and optimized for expression in E. coli cells. This modified molecule also contain 6 histidine residues (SEQ ID NO:10) on the N-terminal end. Histidine residues are used to purify the molecule on a Ni+-column. The gene was cloned into pET21a vector, a commercially available vector used to express gene and make protein in E. coli. BL21 (DE3) cells E. coli where then transformed with the plasmid containing the modified B19 gene. A 250 ml culture was grown in expression of the gene induced by a commercially available medium called of MAGIC MEDIUM. After 24 h, the culture was pelleted by centrifugation. The pellet was then dissolved in 8M Urea solution (8M Urea, 500 mM NaCl, 50 mM Tris-HCl [pH 8.0]) for 3 hrs at 37 dC after having been frozen and thawed three times. The solution was pelleted and the liquid (solubilized protein) was run over a Ni+-column and the purified protein eluted off. This protein was then dialyzed against decreasing concentrations of Urea (6M, 4M, 2M and then 1M and then straight PBS). Protein was dialyzed at 4 dC or room temperature. The resultant protein was run on an SDS-PAGE gel and revealed a protein of the estimated size. This protein was then used to neutralize type I IFN in the 293:IFN assay. We found the purified protein from E. coli was less effective against neutralizing both IFN-alpha and beta compared to mammalian cell expressed, yet nonetheless, the purified protein could neutralize type I IFN and was considered to have value.

SUMMARY

Here, we removed the cell-binding domain from the IFN-binding protein, and discovered that the IFN neutralization domain of the orthopoxvirus IBM is soluble in cell tissues and maintains independent utility. The IFN neutralizing domain, relieved of its cell-binding function, is a novel invention constituting a fully soluble broad-based inhibitor of Type I IFNs from a wide variety of species with in vitro and in vivo utility centered on uses where inhibition of Type I IFN is important. We unexpectedly found that the IFN-binding region, without either the cell-binding region or the signal sequence, was able to fold sufficiently properly, and that there was still IFN neutralizing activity. As is well known, proteins fold in a very specific manner such that removing one of the Ig-like domains may have disrupted binding and IFN neutralization. However, our modified INF-binding protein functioned in vitro and in vivo.

REFERENCES

The publications cited below are incorporated by reference and in their entirety into this patent application.

1. Alcami, A., and G. L. Smith. 1992. A soluble receptor for interleukin-1 beta encoded by Vaccinia virus: a novel mechanism of virus modulation of the host response to infection. Cell 71:153-67.
2. Alcami, A., J. A. Symons, and G. L. Smith. 2000. The Vaccinia virus soluble alpha/beta interferon (IFN) receptor binds to the cell surface and protects cells from the antiviral effects of IFN. J Virol 74:11230-9.
3. Ank, N., H. West, C. Bartholdy, K. Eriksson, A. R. Thomsen, and S. R. Paludan. 2006. Lambda interferon (IFN-lambda), a Type III IFN, is induced by viruses and IFNs and displays potent antiviral activity against select virus infections in vivo. J Virol 80:4501-9.
4. Colamonici, O. R., P. Domanski, S. M. Sweitzer, A. Lamer, and R. M. Buller. 1995. Vaccinia virus B18R gene encodes a Type I interferon-binding protein that blocks interferon alpha transmembrane signaling. J Biol Chem 270:15974-8.
5. Haller, O., G. Kochs, and F. Weber. 2007. Interferon, Mx, and viral countermeasures. Cytokine Growth Factor Rev 18:425-33.
6. Haller, O., G. Kochs, and F. Weber. 2006. The interferon response circuit: induction and suppression by pathogenic viruses. Virology 344:119-30.
7. Hooper, J. W., K. I. Kamrud, F. Elgh, D. Custer, and C. S. Schmaljohn. 1999. DNA vaccination with hantavirus M segment elicits neutralizing antibodies and protects against seoul virus infection. Virology 255:269-78.
8. Kamrud, K. I., J. W. Hooper, F. Elgh, and C. S. Schmaljohn. 1999. Comparison of the protective efficacy of naked DNA, DNA-based Sindbis replicon, and packaged Sindbis replicon vectors expressing Hantavirus structural genes in hamsters. Virology 263:209-19.
9. Nguyen, D. N., P. Kim, L. Martinez-Sobrido, B. Beitzel, A. Garcia-Sastre, R. Langer, and D. G. Anderson. 2009. A novel high-throughput cell-based method for integrated quantification of Type I interferons and in vitro screening of immunostimulatory RNA drug delivery. Biotechnol Bioeng 103:664-75.
10. Novelli, F., and J. L. Casanova. 2004. The role of IL-12, IL-23 and IFN-gamma in immunity to viruses. Cytokine Growth Factor Rev 15:367-77.
11. Pestka, S., C. D. Krause, and M. R. Walter. 2004. Interferons, interferon-like cytokines, and their receptors. Immunol Rev 202:8-32.
12. Symons, J. A., A. Alcami, and G. L. Smith. 1995. Vaccinia virus encodes a soluble Type I interferon receptor of novel structure and broad species specificity. Cell 81:551-60.
13. Weber, F., G. Kochs, and O. Haller. 2004. Inverse interference: how viruses fight the interferon system. Viral Immunol 17:498-515.
14. Xu, R. H., M. Cohen, Y. Tang, E. Lazear, J. C. Whitbeck, R. J. Eisenberg, G. H. Cohen, and L. J. Sigal. 2008. The orthopoxvirus Type I IFN binding protein is essential for virulence and an effective target for vaccination. J Exp Med 205:981-92.
15. Golden and Hooper. 2010. Evaluating the Orthopoxvirus Type I Interferon-Binding Molecule as a Vaccine Target in the Vaccinia Virus Intranasal Murine Challenge Model. Clinical and Vaccine Immunology. Vol 17, No. 11, pages 1656-1665.
16. U.S. Patent application publication no. US2011/0027282, Kotenko, published Feb. 3, 2011.

The invention claimed is:

1. An isolated soluble Orthopoxvirus Type 1 IFN-binding protein, modified from native Orthopoxvirus Type 1 IFN-binding protein_to remove the cell-binding region present in native Orthopoxvirus Type 1 IFN-binding protein, which IFN-binding protein as modified is soluble so as to be mobile through cell tissues and matrices of a mammal without becoming immobilized by binding to cell surfaces and which is diffusable systemically through a mammal to specifically bind to and neutralize Type I IFNs.

2. The Orthopoxvirus Type 1 IFN-binding protein according to claim 1, which has the sequence of SEQ ID NO:1, or is a homolog of SEQ ID NO:1, and has at least 90% identity to SEQ ID NO:1.

3. The Orthopoxvirus Type 1 IFN-binding protein according to claim 1, wherein the IFN-binding protein is encoded by the nucleic acid sequence of SEQ ID NO:4.

4. The Orthopoxvirus Type 1 IFN-binding protein according to claim 1, wherein the Orthopoxvirus is selected from the group consisting of Vaccinia virus, camelpox virus, ectromelia virus, raccoon poxvirus, skunk poxvirus, Tatera poxvirus, Uasin Gishu virus, Volepox virus, variola virus, Vaccinia monkeypox virus and cowpox virus.

5. The Orthopoxvirus Type 1 IFN-binding protein according to claim 1, which protein is modified Vaccinia virus B18/B19 protein.

6. The Orthopoxvirus Type 1 IFN-binding protein according to claim 1, which further comprises a foreign mammalian secretion signal sequence.

7. The Orthopoxvirus Type 1 IFN-binding protein according to claim 6, wherein the foreign mammalian secretion signal sequence is selected from the group consisting of tPA-secretion signal and Ig kappa chain leader sequence.

8. The Orthopoxvirus Type 1 IFN-binding protein according to claim 1, wherein the IFN-binding protein is further modified from native Orthopoxvirus Type 1 IFN-binding protein to remove the signal sequence present in native Orthopoxvirus Type 1 IFN-binding protein.

9. The Orthopoxvirus Type 1 IFN-binding protein according to claim 8, which has the sequence of SEQ ID NO:2, or is a homolog of SEQ ID NO:2, and has at least 90% identity to SEQ ID NO:2.

10. The Orthopoxvirus Type 1 IFN-binding protein according to claim 8, wherein the IFN-binding protein is encoded by the nucleic acid sequence of SEQ ID NO:5.

* * * * *